(12) United States Patent
Josse et al.

(10) Patent No.: US 9,757,250 B2
(45) Date of Patent: Sep. 12, 2017

(54) SPINAL IMPLANT SYSTEM AND METHOD

(71) Applicant: Warsaw Orthopedic, Inc., Warsaw, IN (US)

(72) Inventors: Loic Josse, Yens Vaud (CH); Philippe Lemaitre, Crozet (FR); Jean Charles Le Huec, Pessac (FR); Jorg Franke, Magdeburg (DE)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

(21) Appl. No.: 14/853,691

(22) Filed: Sep. 14, 2015

(65) Prior Publication Data

US 2017/0071753 A1 Mar. 16, 2017

(51) Int. Cl.
| | |
|---|---|
| *A61F 2/44* | (2006.01) |
| *A61B 17/70* | (2006.01) |
| *A61F 2/46* | (2006.01) |
| *A61F 2/30* | (2006.01) |
| *A61F 2/28* | (2006.01) |

(52) U.S. Cl.
CPC .............. *A61F 2/4611* (2013.01); *A61F 2/44* (2013.01); *A61F 2/4637* (2013.01); *A61F 2/30744* (2013.01); *A61F 2002/2835* (2013.01); *A61F 2002/30507* (2013.01); *A61F 2002/30538* (2013.01); *A61F 2002/30551* (2013.01); *A61F 2002/30558* (2013.01); *A61F 2002/30561* (2013.01); *A61F 2002/30601* (2013.01); *A61F 2002/30616* (2013.01); *A61F 2002/30677* (2013.01); *A61F 2002/30784* (2013.01); *A61F 2002/30841* (2013.01); *A61F 2002/4627* (2013.01); *A61F 2002/4628* (2013.01); *A61F 2002/4638* (2013.01)

(58) Field of Classification Search
CPC . A61F 2/4425; A61F 2/4611; A61F 2002/443
USPC .......... 623/17.11, 17.14–17.16; 606/246, 90, 606/99, 105, 86 A
See application file for complete search history.

(56) References Cited

U.S. PATENT DOCUMENTS

| | | | | |
|---|---|---|---|---|
| 2002/0082695 | A1* | 6/2002 | Neumann | A61F 2/44 623/17.11 |
| 2007/0191954 | A1* | 8/2007 | Hansell | A61F 2/442 623/17.15 |
| 2011/0218631 | A1* | 9/2011 | Woodburn, Sr. | A61F 2/44 623/17.16 |
| 2012/0179255 | A1* | 7/2012 | DeFalco | A61F 2/44 623/17.11 |
| 2012/0197403 | A1* | 8/2012 | Merves | A61F 2/44 623/17.16 |

(Continued)

*Primary Examiner* — Pedro Philogene
*Assistant Examiner* — David C Comstock

(57) ABSTRACT

A spinal implant includes a first member defining a longitudinal axis and including a wall that defines an axial cavity. The first member further defines at least one lateral cavity configured for disposal of an instrument and is oriented transverse relative to the longitudinal axis. A second member includes an axial surface defining gear teeth and being configured for disposal with the axial cavity such that the teeth are offset from the longitudinal axis. The instrument is engageable with the teeth to axially translate the second member relative to the first member. Surgical instruments, systems and methods are disclosed.

20 Claims, 27 Drawing Sheets

(56) References Cited

U.S. PATENT DOCUMENTS

| | | | |
|---|---|---|---|
| 2012/0232660 A1* | 9/2012 | Davenport | A61F 2/44 623/17.16 |
| 2012/0265303 A1* | 10/2012 | Refai | A61F 2/44 623/17.11 |
| 2013/0006359 A1* | 1/2013 | Fedorov | A61F 2/4465 623/17.16 |
| 2014/0107787 A1* | 4/2014 | Stinchfield | A61F 2/44 623/17.16 |
| 2014/0156006 A1* | 6/2014 | Bannigan | A61F 2/44 623/17.15 |

* cited by examiner

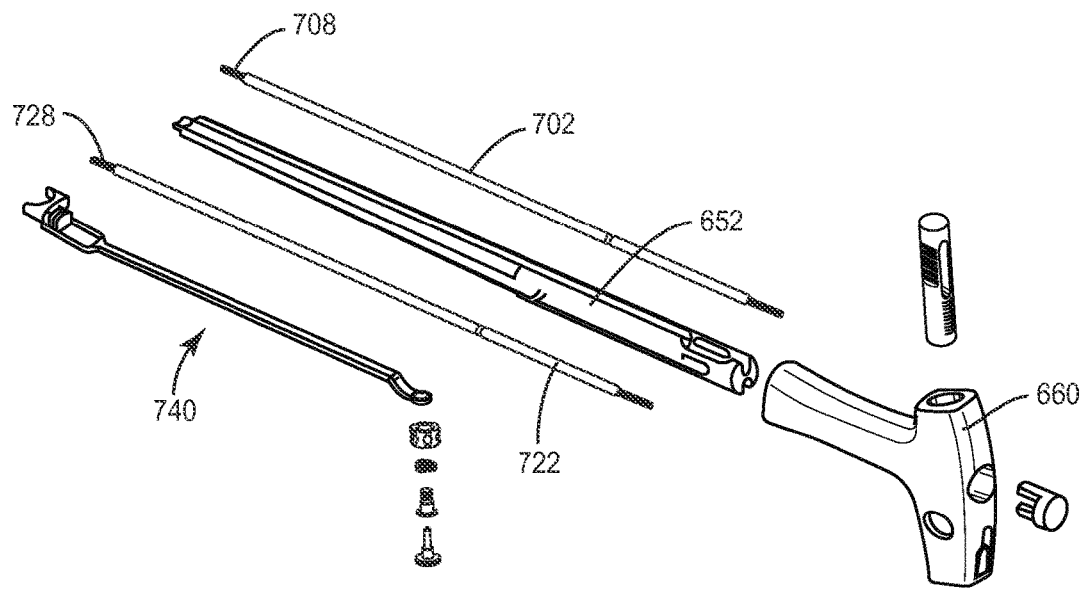
*FIG. 27*
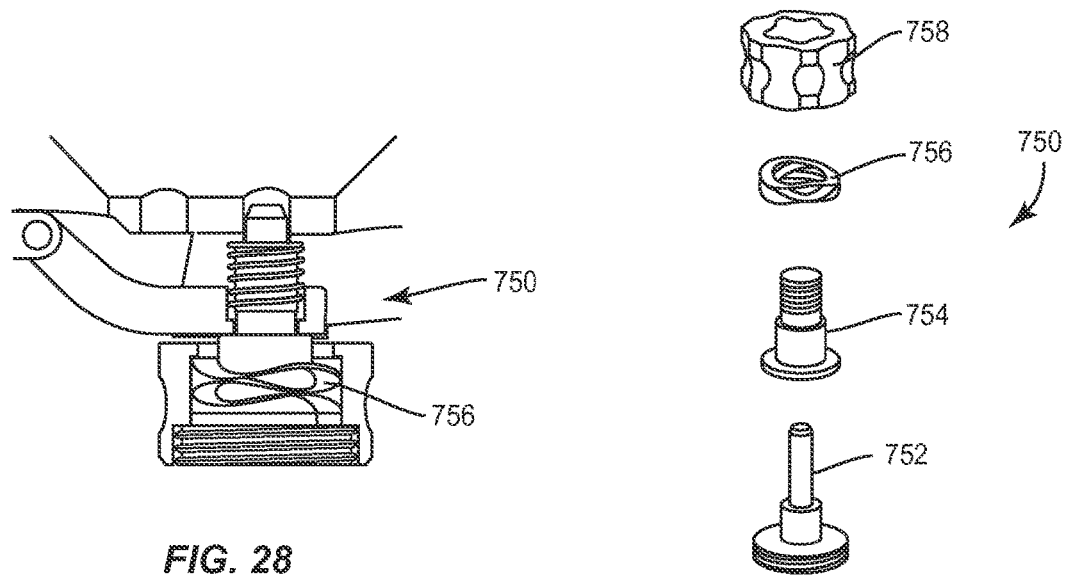
*FIG. 28*
*FIG. 29*

SPINAL IMPLANT SYSTEM AND METHOD

TECHNICAL FIELD

The present disclosure generally relates to medical devices for the treatment of musculoskeletal disorders, and more particularly to a surgical system that includes a spinal implant and a method for treating a spine.

BACKGROUND

Spinal disorders such as degenerative disc disease, disc herniation, osteoporosis, spondylolisthesis, stenosis, scoliosis and other curvature abnormalities, kyphosis, tumor, and fracture may result from factors including trauma, disease and degenerative conditions caused by injury and aging. Spinal disorders typically result in symptoms including pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes fusion, fixation, corpectomy, discectomy, laminectomy and implantable prosthetics. In procedures, such as, for example, corpectomy and discectomy, fusion and fixation treatments may be performed that employ implants to restore the mechanical support function of vertebrae. This disclosure describes an improvement over these prior technologies.

SUMMARY

In one embodiment, a spinal implant is provided. The spinal implant includes a first member defining a longitudinal axis and including a wall that defines an axial cavity. The first member further defines at least one lateral cavity configured for disposal of an instrument and is oriented transverse relative to the longitudinal axis. A second member includes an axial surface defining gear teeth and being configured for disposal with the axial cavity such that the teeth are offset from the longitudinal axis. The instrument is engageable with the teeth to axially translate the second member relative to the first member. In some embodiments, surgical instruments, systems and methods are disclosed.

BRIEF DESCRIPTION OF THE DRAWINGS

The present disclosure will become more readily apparent from the specific description accompanied by the following drawings, in which:

FIG. 27 is a perspective view of components of one embodiment of a surgical system in accordance with the principles of the present disclosure with parts separated;

FIG. 28 is an enlarged, cutaway view of components of the surgical system shown in FIG. 27;

FIG. 29 is a side view of components of the surgical system shown in FIG. 28 with parts separated;

DETAILED DESCRIPTION

Figure 1:
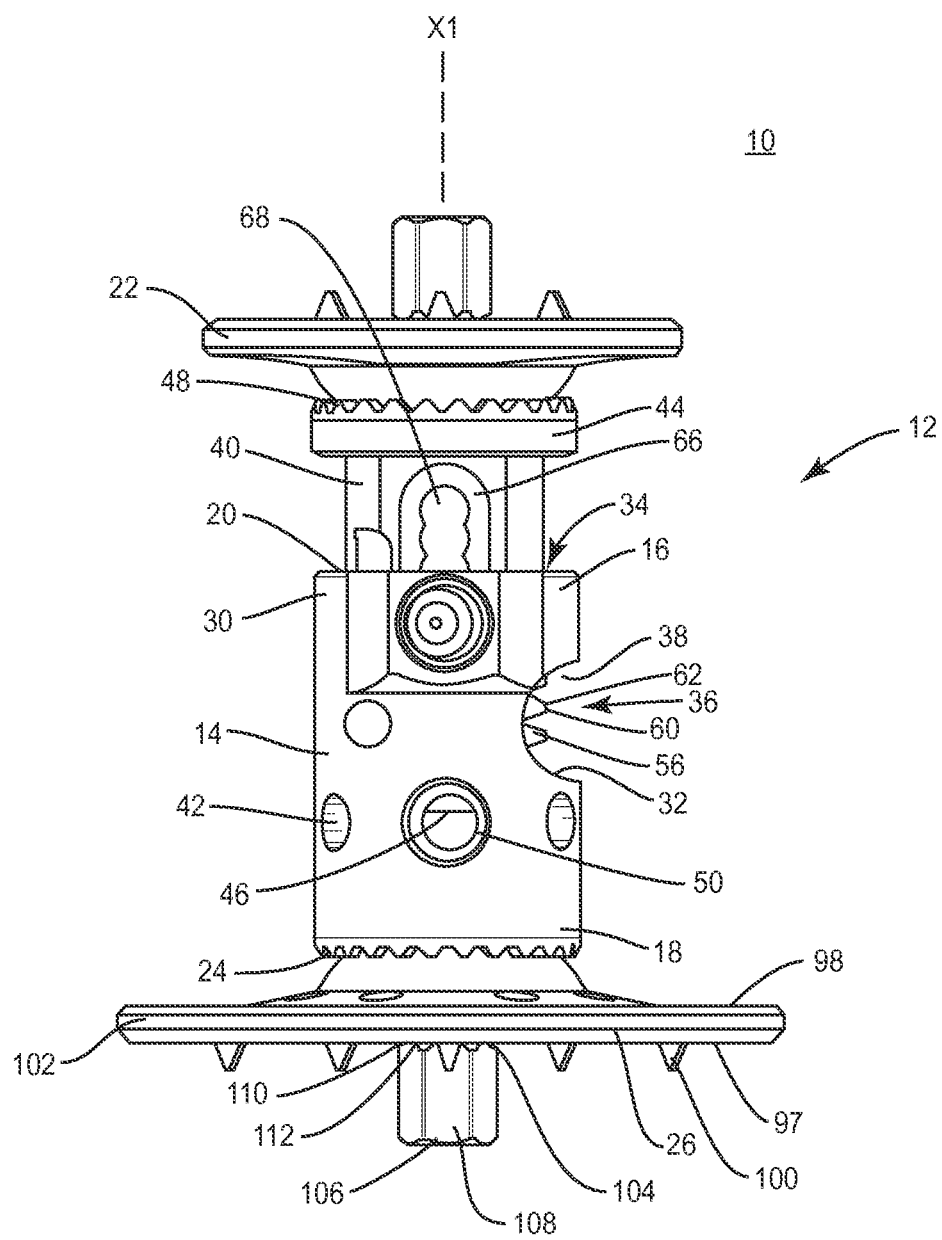
FIG. 1 is a side view of components of one embodiment of a surgical system in accordance with the principles of the present disclosure.
Figure 2:
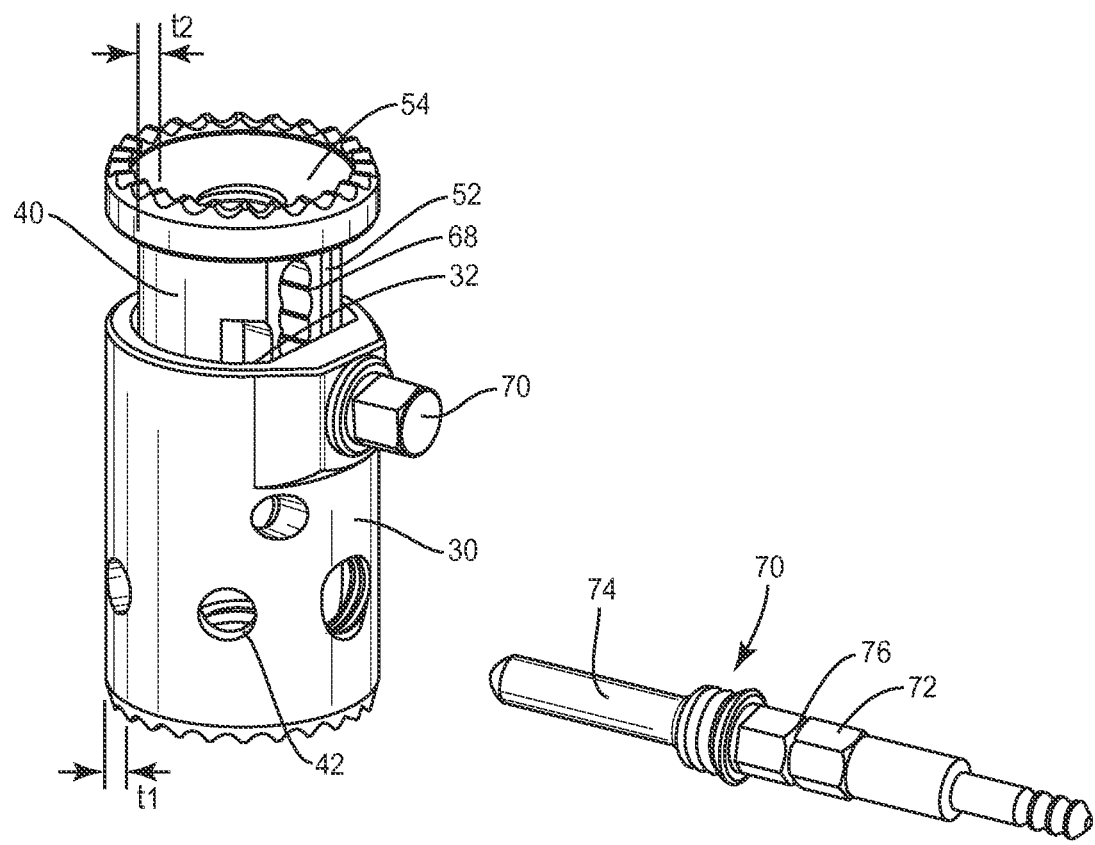
FIG. 2 is a perspective view of components of one embodiment of a surgical system in accordance with the principles of the present disclosure with parts separated.

The exemplary embodiments of the surgical system and related methods of use disclosed are discussed in terms of medical devices for the treatment of musculoskeletal disorders and more particularly, in terms of a surgical system that includes an expandable and/or contractible spinal implant and a method for treating a spine.

In some embodiments, the surgical system includes a spinal implant, such as, for example, a reduced diameter vertebral body replacement device and a surgical instrument, such as, for example, an inserter instrument. In some embodiments, the surgical system includes a spinal implant, such as, for example, a corpectomy/vertebral body replacement (VBR) device that utilizes a surgical instrument, such as, for example, an external pinion mechanism on an inserter to engage a toothed rack on the VBR device. In some embodiments, the diameter of the VBR device is greater than 13 millimeters (mm). In some embodiments, the diameter of the VBR device is 12 mm. In some embodiments, the reduced diameter VBR device includes a reduced diameter due to a rack of the device being placed off center in the VBR device, which is accessible via a side window to an external pinion drive of a surgical instrument. In some embodiments, the side window is a bilateral window. In some embodiments, the window is a uni-lateral window that facilitates reducing the volume of the VBR device. In some embodiments, the uni-lateral window is configured to increase the strength of the VBR device. In some embodiments, the window is a uni-lateral window that facilitates engagement with an inserter instrument.

In some embodiments, the surgical system includes a surgical instrument, such as, for example, a VBR inserter/expander that includes a tilt element. In some embodiments, the VBR inserter/expander includes a pistol grip. In some embodiments, the VBR inserter/expander includes multiple holes in a proximal end to guide a surgical instrument, such as, for example, a multi-use driver. In some embodiments, a surgical instrument, such as, for example, an inserter includes an external ratcheting/quick release to hold VBR device expansion and/or collapsing of the VBR device, for example, if replacement of the VBR device is desired. In some embodiments, the VBR inserter/expander includes a tilt, a pistol grip, multiple holes in a proximal end to guide a multi-use driver, and/or an external ratcheting/quick release.

In some embodiments, the VBR device is expandable. In some embodiments, the VBR device includes a centerpiece. In some embodiments, the centerpiece is configured to engage an endplate. In some embodiments, the centerpiece has a height without the endplate. In some embodiments, the surgical system comprises a kit including a plurality of VBR devices and the height of the centerpiece without the endplate has a first size of 20 to 25 mm. In some embodiments, the height of the centerpiece without the endplate has a second size of 22.5 to 30 mm. In some embodiments, the height of the centerpiece without the endplate has a third size of 28 to 40.5 mm. In some embodiments, the height of the centerpiece without the endplate has a fourth size of 36.5 to 58 mm. In some embodiments, the height of the centerpiece without the endplate has a fifth size of 52.5 to 76.5 mm. In some embodiments, the height of the centerpiece with the endplate is an additional 3.7 mm. In some embodiments, the surgical system includes one or more lock screws with a break-off section.

In some embodiments, the surgical system comprises a kit including a plurality of VBR devices and the endplate has various dimensions. In some embodiments, the dimensions of the endplate are 21.5 mm long and 13.5 mm wide. In some embodiments, the dimensions of the endplate are 30 mm long and 18.5 mm wide. In some embodiments, the dimensions of the endplate are 42 mm long and 26 mm wide. In some embodiments, the endplate has a textured surface. In some embodiments, the textured surface is toothed or barbed. In some embodiments, the endplate includes holes or openings defined by the surface of the endplate. In some embodiments, the endplate is fixed to an end of the centerpiece via a screw. In some embodiments, the screw includes a break-off section.

In some embodiments, the surgical system includes a surgical instrument, such as, for example, a template. In some embodiments, the template is configured to engage with an end of an inserter instrument. In some embodiments, the template and an opposing end of the inserter instrument creates an angle. In some embodiments, the angle is 10 degrees. In some embodiments, the template and the inserter instrument engage at an end via a bearing. In some embodiments, the template and the inserter instrument engage via a 0 degree angle. In some embodiments, the template and the inserter instrument engage via a 45 degree angle. In some embodiments, the template and the inserter instrument engage via a 90 degree angle. In some embodiments, the template has various dimensions. In some embodiments, the dimensions of the template are 42 mm long and 26 mm wide.

In some embodiments, the dimensions of the template are 30 mm long and 18.5 mm wide. In some embodiments, the dimensions of the template are 21.5 mm long and 13.5 mm wide.

In some embodiments, the surgical system includes a surgical instrument, such as, for example, a sizer. In some embodiments, the sizer includes a locking lever to lock the sizer in a closed position. In some embodiments, the sizer includes visual indicia. In some embodiments, a practitioner may select an appropriate VBR device range via the indicia. In some embodiments, the appropriate VBR device range is selected without endplates.

In some embodiments, the surgical system includes a surgical instrument, such as, for example, an inserter that is configured for direct driving expansion and/or collapse of a VBR device. In some embodiments, the inserter's overall length is shortened. In some embodiments, the inserter provides accuracy of a locking screw alignment with the centerpiece and for easier insertion. In some embodiments, the inserter has a reduced number of parts for cleaning components. In some embodiments, the inserter includes a position of the release button configured to prevent mishandling. In some embodiments, the inserter includes a direct driving expansion. In some embodiments, the inserter includes a tactile feel of distraction forces. In some embodiments, the inserter provides a reduction of potential misalignment due to a limited number of components.

In some embodiments, the inserter includes a locking screw driver. In some embodiments, the locking screw driver includes visual confirmation via visual indicia of a locking screw tightening. In some embodiments, the locking screw driver includes a locking screw retaining feature. In some embodiments, the inserter includes a T-handle that is disposed at an end of the inserter. In some embodiments, the inserter is guided continuously to the VBR device.

In some embodiments, the surgical system includes a surgical instrument, such as, for example, a short nut-driver. In some embodiments, the nut-driver is configured for a dual purpose. In some embodiments, the dual purpose of the nut-driver includes the nut-driver as an expansion driver and the nut-driver as an endplate setscrew driver.

In some embodiments, the VBR device includes titanium 12 mm diameter centerpieces, flat endplates and an implant inserter instrument. In some embodiments, the centerpiece is titanium with a 12 mm diameter. In some embodiments, the centerpiece includes a large size range and includes multiple approaches. In some embodiments, the surgical system includes an implant inserter instrument. In some embodiments, the surgical system includes an anatomical titanium endplate.

In some embodiments, the surgical system includes a vertebral body replacement system. In some embodiments, the vertebral body replacement system is employed with a method for treating single or multiple vertebral levels in a cervical and/or thoracolumbar spine to replace a collapsed, damaged, or unstable vertebral body due to tumor or trauma. In some embodiments, the vertebral body replacement system includes a series of endplates that are attached to a series of centerpieces to form a complete construct to accommodate different anatomical spine regions. In some embodiments, the vertebral body replacement system includes two or more endplate options, which include flat or anatomic configurations. In some embodiments, an implant inserter instrument will permit angling the VBR device for mini-invasive approaches, to straighten and to expand.

In some embodiments, the surgical system comprises a VBR device having titanium 12 mm diameter centerpieces, flat endplates and an implant inserter instrument. In some embodiments, the surgical system includes a titanium 12 mm diameter centerpiece. In some embodiments, the centerpiece includes threaded holes configured for endplate attachment. In some embodiments, the centerpiece is translatable and is configured for reversible expansion. In some embodiments, the centerpiece includes a dual expansion rack. In some embodiments, the dual expansion rack includes a primary set of teeth configured for use without endplates in the cervical and/or upper thoracic spine. In some embodiments, a locking break-off nut is disposed transversely within an opening/hole on a side of the centerpiece. In some embodiments, the centerpiece includes openings/holes that are threaded and configured for instrument connection. In some embodiments, the openings/holes are configured for bone fusion assessment.

In some embodiments, the centerpiece is configured to be formed in various sizes/dimensions. In some embodiments, the range of the dimensions of the centerpiece include but are not limited to a height of 15.5 mm and a width of 23.5 mm, a height of 23 mm and a width of 32 mm, a height of 28 mm and a width of 44 mm, a height of 42 mm and a width of 58 mm, a height of 56 mm and a width of 72 mm, and a height of 70 mm and a width of 86 mm. In some embodiments, when the endplate is disposed at an end of the centerpiece, the height of the combination of the centerpiece and the endplate is an additional 4 mm and includes a connection where the endplate is translatable at an angle of 10 degrees in all directions. In some embodiments, when an endplate is disposed at a proximal end and a distal end of the centerpiece, the height of the combination of the centerpiece and the endplates is an additional 4 mm for each end and includes a connection where the endplates are translatable at an angle of more or less than 10 degrees in all directions.

In some embodiments, the surgical system includes a series of flat endplates that can be attached to a series of centerpieces to form a complete construct. In some embodiments, an overall diameter of the centerpiece is 12 mm in diameter and facilitates implantation into a cervical and thoraco-lumbar spinal region. In some embodiments, a primary set of teeth are disposed on both ends of the centerpiece for implantation of the centerpiece without one or two endplates. In some embodiments, the centerpiece is expandable and expansion is locked by a locking break-off screw. In some embodiments, the locking break-off screw provides a controlled torque tightening.

In some embodiments, the endplate is flat. In some embodiments, the range of the dimensions of the endplate include but are not limited to a diameter of 12 mm, a 14 mm length and a 16 mm width, a 18 mm length and a 22 mm width, and a 24 mm length and a 29 mm width. In some embodiments, the endplate has a 360 degree adjustment when attached to an end of the centerpiece. In some embodiments, when the endplate/endplates are connected to the centerpiece, they are translatable at an angle of more or less than 10 degrees in all directions. In some embodiments, the endplate can be positioned into a surgical site anteriorly, laterally, obliquely, posteriorly and/or postero-laterally, for example, to be employed with a transforaminal lumbar interbody fusion (TLIF).

In some embodiments, the surgical system includes an implant inserter instrument. In some embodiments, the implant inserter instrument is configured to move via one rotation of a knob incrementally. In some embodiments, rotation of the knob is equivalent to one increment, which is 2 mm.

In some embodiments, the surgical system includes a dual purpose screwdriver, an implant inserter instrument and a lateral knob. In some embodiments, the implant inserter instrument allows implant insertion and provides an oblique angle for minimally invasive approaches. In some embodiments, the implant inserter instrument is moved in an upward direction in between two vertebrae and expanded. The expansion is performed by acting on a gear rack that is actuated by a lateral knob. The dual purpose screwdriver facilitates VBR attachment/un-attachment and is disposed on the implant inserter instrument for screwing/unscrewing of the locking break-off screw.

In some embodiments, the surgical system includes an anatomical titanium endplate with a ball and socket joint formed from a surface of the endplate and is configured to adapt the VBR device to different surgical approaches. In some embodiments, the surface of the endplate is textured with ribs to improve stiffness of the endplate. In some embodiments, hex holes are disposed in the surface of the endplate to facilitate bone to bone contact, thereby enhancing fusion rate.

In some embodiments, the surgical system includes an anatomical titanium endplate produced via a selective laser sintering (SLS) process or an electron beam melting (EBM) process from titanium powder. These processes allow the endplate to be manufactured in a single piece and also allow the endplate to be divided into different design spaces. In some embodiments, the endplate includes a solid design space and a porous lattice design space. In some embodiments, the solid design space of the endplate is treated as a solid for manufacture and the porous lattice design space is treated as a design space for trabecular lattice creation. In some embodiments, the SLS and EBM processes offer the possibility to manufacture endplates with osseointegration surfaces in a single phase. In some embodiments, there is structural continuity between solid and porous sections. In some embodiments, the endplate includes windows configured to allow bone to bone contact, thereby enhancing fusion rate. In some embodiments, the endplate includes a surface including a porous region and a solid region.

In some embodiments, the surgical system includes an anatomical titanium endplate having a full porous surface configured to improve a contact area to bone, and to facilitate penetration through the solid region to enhance fusion rate. In some embodiments, the surgical system includes an anatomical titanium endplate having a solid region and a porous region that do not have the same thickness. In some embodiments, the thickness of the porous region is 0.5 mm thick and the solid region is 0.3 mm thick. In some embodiments, the porous region is 0.6 mm thick and the solid region is 0.6 mm thick.

In some embodiments, the surgical system includes a conical setscrew configured for expansion of the VBR device between 5.5 mm and 8 mm bilaterally. In some embodiments, the surgical system includes an endplate that includes bone teeth that are configured for bone engagement. The endplate is configured for lateral translation. In some embodiments, the surgical system includes an endplate configured for a spherical connection with a cam of a VBR device. In some embodiments, the surgical system includes an endplate configured for a pivot connection with a cam of a VBR device. In some embodiments, the cam can be used without the endplate. In some embodiments, the inserter instrument includes a channel for cam insertion. In some embodiments, the instrument includes teeth engagement between the instrument and the cam. In some embodiments, the cam pivots at an angle of 60 degrees relative to the instrument.

In some embodiments, the centerpieces are configured to expand from 0 to 30 mm via increments of 5 mm. In some embodiments, the centerpieces are stabilized with a cross pin. In some embodiments, the cross pin engages the centerpiece transversely via a channel. In some embodiments, expansion is initiated by an implant inserter instrument. In some embodiments, the diameter of the centerpiece is 14 mm. In some embodiments, the centerpiece is manufactured from PEEK material.

In some embodiments, the surgical system includes endplates that are manufactured from a titanium alloy material. In some embodiments, a bearing surface facilitates engagement of an endplate and an end of a centerpiece. In some embodiments, the bearing surface includes two locking screws. In some embodiments, the bearing surface facilitates translation of the endplate at an adaptable angle of more or less than 15 degrees relative to the centerpiece. In some embodiments, the endplate includes a large or medium core. In some embodiments, the centerpiece, endplate and/or endplates are inserted into the surgical site via multiple approaches. In some embodiments, the centerpiece, endplate and/or endplates are inserted into the surgical site anteriorly, laterally, obliquely, posteriorly and/or postero-laterally, for example, to be employed with a TLIF. In some embodiments, the endplate can be adjusted 360 degrees.

In some embodiments, the surgical system includes an additional implant to the VBR implant. In some embodiments, the implant allows bone graft insertion around the VBR. In some embodiments, the implant is disposed anteriorly or posteriorly. In some embodiments, the implant is a bone graft container.

In some embodiments, the surgical system includes an in situ attachable bone graft partition for attachment to a small diameter VBR device. In some embodiments, the in situ attachable bone graft partition prevents bone graft from migrating out the posterior side of the spine after a corpectomy procedure.

In some embodiments, the surgical system includes a bone graft container. In some embodiments, the bone graft container is filled with bone graft and is used in conjunction with large bone resection. In some embodiments, the bone graft container is used only with anterior or lateral surgery.

In some embodiments, the surgical system includes a combination inserter and expander instrument made from titanium. In some embodiments, the instrument includes a nut driver. In some embodiments, the instrument includes a lateral knob. In some embodiments, the nut driver includes a long shaft. In some embodiments, the long shaft includes three different outer diameters. In some embodiments, the instrument includes a knob.

In some embodiments, a method of manufacturing the surgical system is provided. The method includes the reduction of milling steps. In some embodiments, the method includes the alignment of holes and/or grooves. In some embodiments, the method gives priority to turning versus milling operations.

In some embodiments, the instrument includes a rack. In some embodiments, the rack is not needed and the surgical system includes only two implant positions. In some embodiments, the two implant positions are at 0 degrees and 60 degrees. In some embodiments, the instrument includes spring blades. In some embodiments, the spring blades are not mandatory.

In some embodiments, the instrument includes a handle configured for dual gripping ability. In some embodiments, the instrument includes an index button that is entirely dismountable. In some embodiments, the instrument includes a knob to prevent damage on a part of the instrument. In some embodiments, the surgical system includes a combination inserter and expander instrument. In some embodiments, the instrument is locked in a flipped position and a straight position via a pressure screw. In some embodiments, the surgical system includes a variable angle inserter instrument. In some embodiments, the surgical system includes an instrument set. In some embodiments, the instrument set includes a nut driver, a spur gear key and a variable angle VBR expander.

In some embodiments, the variable angle VBR expander includes graduations to access expansion height. In some embodiments, the variable angle VBR expander includes toothed gears and gear shafts. In some embodiments, the gear shafts are symmetrical. In some embodiments, the variable angle VBR expander includes a handle. In some embodiments, the handle is titanium and is configured for weight optimization. In some embodiments, the gear shaft provides up to 60 degrees of angulation.

In some embodiments, the instrument can be dismantled for cleaning. In some embodiments, screws from the handle are removed. A push button and two springs disposed in the handle are then pulled in a backward direction and a long connecting bar is rotated. The gear shafts are then removed. In some embodiments, the instrument includes a fenestrated ratchet. In some embodiments, the fenestrated ratchet provides cleaning access.

In some embodiments, the nut driver of the instrument is configured for three functions. In some embodiments, the nut driver is configured for implant connection to the VBR expander. In some embodiments, the nut driver is configured for VBR locking after expansion. In some embodiments, the nut driver is configured for endplate tightening. In some embodiments, the spur gear key of the instrument is configured for a right-handed and/or left-handed person.

In some embodiments, the surgical system includes a variable angle inserter instrument. In some embodiments, the surgical system includes an instrument set. In some embodiments, the instrument set includes an impaction head, a spur gear key, a variable angle VBR expander, a nut driver and a short nut driver.

In some embodiments, the instrument is configured for implant expansion. In some embodiments, a spur gear key is positioned on multiple sides of the expander. In some embodiments, the spur gear key is positioned on a top side of the expander. In some embodiments, the spur gear key is positioned on a transverse side relative to the top side of the expander. In some embodiments, the spur gear key is rotated in a direction to facilitate expansion of the implant. In some embodiments, the implant expansion is up to 16 mm. In some embodiments, the instrument includes visual indicia to indicate a height of expansion. In some embodiments, expansion is unlocked when an implant is perpendicular. In some embodiments, the instrument locks the implant in place. In some embodiments, the instrument is configured to unlock and collapse the implant.

In some embodiments, one or all of the components of the surgical system are disposable, peel-pack, pre-packed sterile devices used with an implant. One or all of the components of the surgical system may be reusable. The surgical system may be configured as a kit with multiple sized and configured components.

In some embodiments, the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the present disclosure may be employed with other osteal and bone related applications, including those associated with diagnostics and therapeutics. In some embodiments, the disclosed surgical system and methods may be alternatively employed in a surgical treatment with a patient in a prone or supine position, and/or employ various surgical approaches to the spine, including anterior, posterior, posterior mid-line, lateral, postero-lateral, and/or antero-lateral approaches, and in other body regions. The present disclosure may also be alternatively employed with procedures for treating the lumbar, cervical, thoracic, sacral and pelvic regions of a spinal column. The system and methods of the present disclosure may also be used on animals, bone models and other non-living substrates, such as, for example, in training, testing and demonstration.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of a surgical system and related methods of employing the surgical system in accordance with the principles of the present disclosure. Alternate embodiments are also disclosed. Reference is made in detail to the exemplary embodiments of the present disclosure, which are illustrated in the accompanying figures. Turning to FIGS. 1-5, there is illustrated components of a surgical system, such as, for example, a spinal implant system 10.

The components of spinal implant system 10 can be fabricated from biologically acceptable materials suitable for medical applications, including metals, synthetic polymers, ceramics and bone material and/or their composites. For example, the components of spinal implant system 10, individually or collectively, can be fabricated from materials such as stainless steel alloys, commercially pure titanium, titanium alloys. Grade 5 titanium, super-elastic titanium alloys, cobalt-chrome alloys, superelastic metallic alloys (e.g., Nitinol, super elasto-plastic metals), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations.

Various components of spinal implant system 10 may have material composites, including the above materials, to achieve various desired characteristics such as strength, rigidity, elasticity, compliance, biomechanical performance, durability and radiolucency or imaging preference. The components of spinal implant system 10, individually or collectively, may also be fabricated from a heterogeneous material such as a combination of two or more of the above-described materials. The components of spinal implant system 10 may be monolithically formed, integrally connected or include fastening elements and/or instruments, as described herein.

Spinal implant system 10 is employed, for example, with a minimally invasive procedure, including percutaneous techniques, mini-open and open surgical techniques to deliver and introduce instrumentation and/or an implant, such as, for example, a corpectomy implant, at a surgical site within a body of a patient, for example, a section of a spine. In some embodiments, spinal implant system 10 may be employed with surgical procedures, such as, for example, corpectomy and discectomy, which include fusion and/or fixation treatments that employ implants, in accordance with the principles of the present disclosure, to restore the mechanical support function of vertebrae.

Spinal implant system 10 includes a spinal implant 12 having a member, such as, for example, an outer body 14 having a tubular configuration. Body 14 extends in a linear configuration and defines a longitudinal axis X1. In some embodiments, body 14 may extend in alternate configurations, such as, for example, arcuate, offset, staggered and/or angled portions, which may include acute, perpendicular and obtuse. In some embodiments, spinal implant 12 may include a vertebral body replacement device, a corpectomy implant, an interbody cage, an interbody spacer and/or an intervertebral implant.

Body 14 extends between an end 16 and an end 18. End 16 defines an end face 20 that engages inner body 40, as described herein. End 18 defines an end face 24.

Body 14 includes a wall, such as, for example, a tubular wall 30 that defines a substantially average thickness t1. In some embodiments, thickness t1 may be uniform or have alternate dimensions along the length of wall 30, for example, portions having a greater or lesser thickness. Wall 30 includes an inner surface 32 that defines an axial cavity 34 extending between ends 16, 18. In some embodiments, wall 30 includes a cylindrical cross-section. In some embodiments, the cross-section geometry of wall 30 may have various configurations, such as, for example, round, oval, oblong, triangular, polygonal having planar or arcuate side portions, irregular, uniform, non-uniform, consistent, variable, horseshoe shape, U-shape or kidney bean shape. In some embodiments, surface 32 is smooth or even. In some embodiments, surface 32 may be rough, textured, porous, semi-porous, dimpled and/or polished.

Wall 30 includes an inwardly oriented surface that defines a lateral cavity, such as, for example, a side window 36. Window 36 includes an aperture, such as, for example, opening 38. Opening 38 is configured for disposal of an instrument utilized to facilitate expansion and/or collapse of body 14 and a member, such as, for example, an inner body 40 of spinal implant 12, as described herein. Opening 38 has a circular aperture configuration and is oriented for disposal of a surgical instrument, such as, for example, an inserter 150, as described herein, configured for engagement with gear teeth of body 40.

Opening 38 is oriented substantially transverse, such as, for example, perpendicular to axis X1. In some embodiments, opening 38 may be variously oriented relative to axis X1, such as, for example, parallel or angled, which may include acute and obtuse orientations. In some embodiments, wall 30 may include one or a plurality of openings. In some embodiments, opening 38 may be variously configured, such as, for example, oval, oblong, triangular, polygonal having planar or arcuate side portions, irregular, uniform, non-uniform, consistent, variable, horseshoe shape, U-shape or kidney bean shape.

In some embodiments, wall 30 defines openings 42 configured to receive an agent, which may include bone graft (not shown) and/or other materials, as described herein, for employment in a fixation or fusion treatment used for example, in connection with a corpectomy. In some embodiments, body 14 may define one or a plurality of openings 42.

Openings 42 are configured to facilitate the flow of an agent between cavity 34 and exterior to body 14 and adjacent vertebrae, as described herein, to promote bone growth, joint immobilization, therapy and/or treatment. In some embodiments, openings 42 can be oriented and facing a disc space and/or vertebrae. Openings 42 are oriented substantially perpendicular to axis X1. In some embodiments, one or a plurality of openings 42 may be variously oriented relative to axis X1, such as, for example, transverse and/or angled, which may include acute and obtuse orientations.

In some embodiments, the agent may include therapeutic polynucleotides or polypeptides and bone growth promoting material, which can be packed or otherwise disposed on or about the surfaces of the components of spinal implant system 10, including spinal implant 12. The agent may also include biocompatible materials, such as, for example, biocompatible metals and/or rigid polymers, such as, titanium elements, metal powders of titanium or titanium compositions, sterile bone materials, such as allograft or xenograft materials, synthetic bone materials such as coral and calcium compositions, such as hydroxyapatite, calcium phosphate and calcium sulfite, biologically active agents, for example, biologically active agents coated onto the exterior of spinal implant 12 and/or applied thereto for gradual release such as by blending in a bioresorbable polymer that releases the biologically active agent or agents in an appropriate time dependent fashion as the polymer degrades within the patient. Suitable biologically active agents include, for example, bone morphogenic protein (BMP) and cytokines.

In one embodiment, cavity 34 may be configured as a reservoir configured as a drug depot with medication for pain and may include antibiotics and/or therapeutics. In some embodiments, cavity 34 includes active agents and may include one or a plurality of therapeutic agents and/or pharmacological agents for release, including sustained release, to treat, for example, pain, inflammation and degeneration. The agent may include pharmacological agents, such as, for example, antibiotics, anti-inflammatory drugs including but not limited to steroids, anti-viral and anti-retroviral compounds, therapeutic proteins or peptides, therapeutic nucleic acids and combinations thereof.

Body 40 has a tubular configuration and is oriented for disposal within axial cavity 34. Body 40 extends and/or contracts in a linear configuration relative to axis X1. In some embodiments, body 40 may extend in alternate configurations, such as, for example, arcuate, offset, staggered and/or angled portions, which may include acute, perpendicular and obtuse.

Body 40 extends between an end 44 and an end 46. End 44 defines an end face 48 configured to engage vertebral tissue and/or endplate 22, as described herein. In some embodiments, the vertebral tissue may include intervertebral tissue, endplate surfaces and/or cortical bone. In some embodiments, end 44 can include a surface that may be rough, textured, porous, semi-porous, dimpled and/or polished.

Body 40 includes a wall, such as, for example, a tubular wall 52 that defines a substantially average thickness t2. In some embodiments, thickness t2 may be uniform or have alternate dimensions along the length of wall 52, for example, portions having a greater or lesser thickness. Wall 52 includes an inner surface 54 that defines an axial cavity 56 extending between ends 44, 46. In some embodiments, wall 52 includes a cylindrical cross-section. In some embodiments, the cross-sectional geometry of wall 52 may have various configurations, such as, for example, round, oval, oblong, triangular, polygonal having planar or arcuate side portions, irregular, uniform, non-uniform, consistent, variable, horseshoe shape, U-shape or kidney bean shape. In some embodiments, surface 54 is smooth or even. In some embodiments, surface 54 may be rough, textured, porous, semi-porous, dimpled and/or polished. Body 40 is configured for disposal with cavity 34 such that walls 30, 52 are concentric with axis X1.

Wall 52 includes a surface 56. Surface 56 includes a gear rack 60 having a plurality of teeth 62 that are disposed therealong. Teeth 62 are disposed in a linear, serial configuration along surface 56 and in an offset configuration relative to axis X1. Teeth 62 extend into opening 38 to facilitate engagement with a pinion gear 192 of inserter 150 through opening 38, as described herein. Engagement of inserter 150 with teeth 62 axially translates body 40 relative to body 14 between a collapsed configuration and an expanded configuration for disposal in a selected orientation, as described herein.

Wall 52 includes a surface 66 disposed along thickness t2. Surface 66 defines an opening, such as, for example, an axial slot 68. Slot 68 is disposed along axis X1. Slot 68 is configured for engagement with a lock 70, as described herein. In some embodiments, the cross-sectional geometry of slot 68 may have various configurations, such as, for example, round, oval, oblong, triangular, polygonal having planar or arcuate side portions, irregular, uniform, non-uniform, consistent, variable, horseshoe shape, U-shape or kidney bean shape. In some embodiments, surface 66 is smooth, even, rough, textured, porous, semi-porous, dimpled and/or polished. In some embodiments, slot 68 may extend in alternate configurations, such as, for example, arcuate, offset, staggered and/or angled portions, which may include acute, perpendicular and obtuse relative to axis X1.

Lock 70 includes a portion 72 and a portion 74. Portions 72, 74 are connected at a reduced diameter portion 76 that is frangibly connected to portion 74. In some embodiments, portion 74 is configured for a threaded engagement with slot 68. In some embodiments, lock 70 extends through a threaded opening of wall 30 to engage slot 68. In some embodiments, portions 72, 74 are fabricated from a fracturing and/or frangible material such that manipulation of portion 72 relative to portion 74 can fracture and separate portion 72 from portion 74 at a predetermined force and/or torque limit, as described herein. In some embodiments, as force and/or torque is applied to portion 72 and resistance increases, for example, due to fixation of portion 74 with spinal implant 12, as described herein, the predetermined torque and force limit is approached.

In some embodiments, portions 72, 74 can fracture and separate at a predetermined force or torque limit, which may be in a range of approximately 2 Newton meters (N-m) to 8 Nm. In some embodiments, portions 72, 74 may have the same or alternate cross section configurations, may be fabricated from a homogenous material or heterogeneously fabricated from different materials, and/or alternately formed of a material having a greater degree, characteristic or attribute of plastic deformability, frangible property and/or break away quality to facilitate fracture and separation of portions 72, 74.

Endplate 22 is configured for engagement with end 44 of body 40. Endplate 22 extends between a vertebral engaging surface 80 and a surface 82. Surface 80 includes one or a plurality of tissue penetrating members, such as, for example, teeth 84. In one embodiment, one or more teeth 84 may have various configurations, for example, round, oval, rectangular, polygonal, irregular, tapered, offset, staggered, uniform and non-uniform. In some embodiments, surface 80 may be rough, textured, porous, semi-porous, dimpled, knurled, grooved and/or polished to facilitate engagement with tissue. In some embodiments, the vertebral tissue may include intervertebral tissue, endplate surfaces and/or cortical bone.

Figure 4:
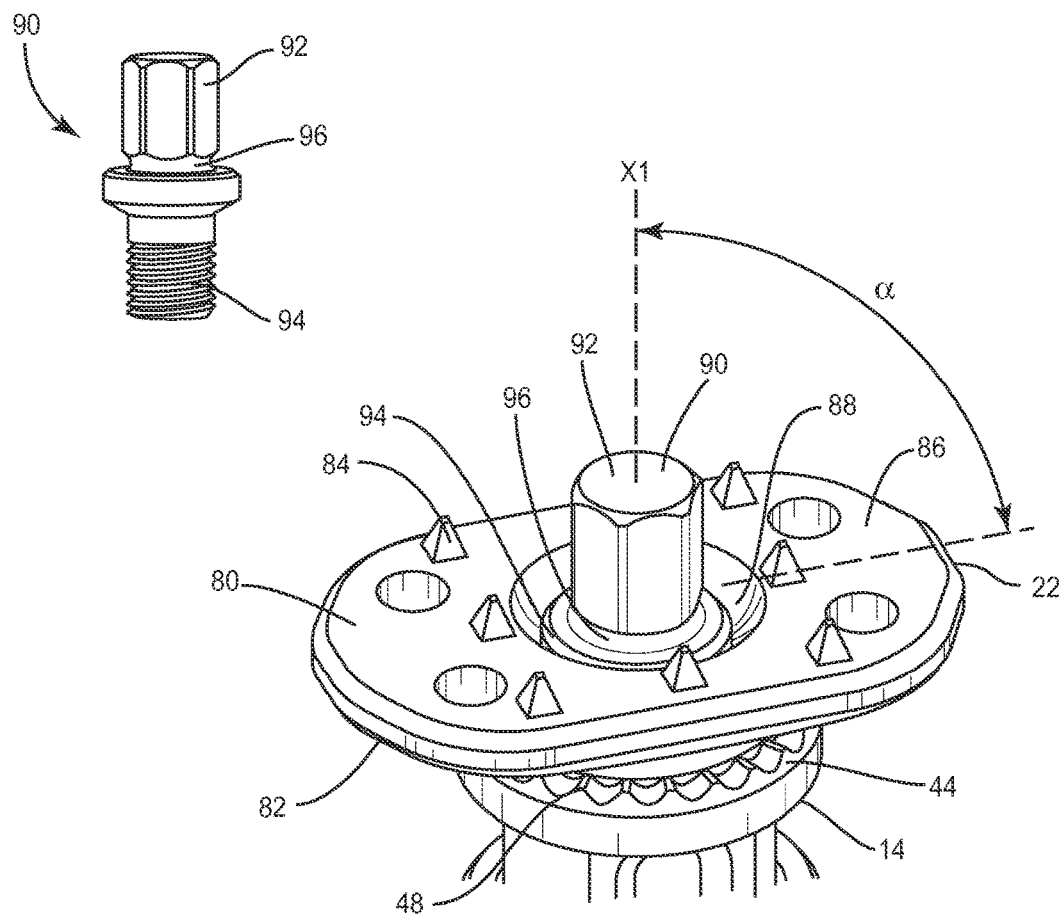
FIG. 4 is a perspective break away view of components of one embodiment of a surgical system in accordance with the principles of the present disclosure with parts separated.

Endplate 22 includes a stratum 86. Stratum 86 includes at least one mating element, such as, for example, an opening 88 configured for engagement with a lock 90 configured for mating engagement with an opening disposed with end face 48, as described herein. In some embodiments, endplate 22 is rotatable about and relative to axis X1 and is moveable in a plurality of angular orientations a relative to axis X1, as shown in FIG. 4. In some embodiments, endplate 22 is moveable relative to axis X1 between a first angular orientation and a second angular orientation. In some embodiments, endplate 22 may be disposed with end 44 for relative movement in orientations relative to axis X1, such as, for example, transverse, perpendicular and/or other angular orientations such as acute or obtuse, co-axial and/or may be offset or staggered. In some embodiments, endplate 22 may move relative to end 44 in alternate planes relative to a body, such as, for example, vertical, horizontal, diagonal, transverse, coronal and/or sagittal planes of a body. In some embodiments, endplate 22 may move relative to end 44 in a multi-axial configuration such that endplate 22 is rotatable to a selected angle through and within an angular range relative to axis X1 in a plurality of planes that lie in a cone configuration.

In some embodiments, stratum 86 includes a solid configuration that increases the strength of endplate 22. In some embodiments, stratum 86 includes an interconnected porous configuration, which facilitates bone ingrowth. In some embodiments, stratum 86 includes one or a plurality of layers. In some embodiments, stratum 86 includes one or a plurality of layers, which may include solid titanium, porous titanium, solid titanium-HA composite (porous titanium completely filled with HA) and/or porous titanium-coated with HA. In some embodiments, the cross-sectional geometry of endplate 22 may have various configurations, such as, for example, round, oval, oblong, triangular, polygonal having planar or arcuate side portions, irregular, uniform, non-uniform, consistent, variable, horseshoe shape, U-shape or kidney bean shape.

Lock 90 includes a portion 92 and a portion 94. Portions 92, 94 are connected at a reduced diameter portion 96 that is tangibly connected to portion 94. In some embodiments, portion 94 is configured for a threaded engagement with end face 48. In some embodiments, portions 92, 94 are fabricated from a fracturing and/or frangible material such that manipulation of portion 92 relative to portion 94 can fracture and separate portion 92 from portion 94 at a predetermined force and/or torque limit, as described herein. In some embodiments, as force and/or torque is applied to portion 92 and resistance increases, for example, due to fixation of portion 94 with spinal implant 12, as described herein, the predetermined torque and force limit is approached.

In some embodiments, portions 92, 94 can fracture and separate at a predetermined force or torque limit, which may be in a range of approximately 2 N-m to 8 N-m. In some embodiments, portions 92, 94 may have the same or alternate cross section configurations, may be fabricated from a homogenous material or heterogeneously fabricated from different materials, and/or alternately formed of a material having a greater degree, characteristic or attribute of plastic deformability, frangible property and/or break away quality to facilitate fracture and separation of portions 92, 94.

Endplate 26 is configured for engagement with end 18 of body 14. Endplate 26 extends between a vertebral engaging surface 97 and a surface 98. Surface 97 includes one or a plurality of tissue penetrating members, such as, for example, teeth 100. In one embodiment, one or more teeth 100 may have various configurations, for example, round, oval, rectangular, polygonal, irregular, tapered, offset, staggered, uniform and non-uniform. In some embodiments, surface 97 may be rough, textured, porous, semi-porous, dimpled, knurled, grooved and/or polished to facilitate engagement with tissue. In some embodiments, the vertebral tissue may include intervertebral tissue, endplate surfaces and/or cortical bone.

Endplate 26 includes a stratum 102. Stratum 102 includes at least one mating element, such as, for example, an opening 104 configured for engagement with a lock 106 configured for mating engagement with an opening disposed with end face 24, as described herein. In some embodiments, endplate 26 is rotatable about and relative to axis X1 and is moveable in a plurality of angular orientations relative to axis X1, similar to that described herein. In some embodiments, endplate 26 is moveable relative to axis X1 between a first angular orientation and a second angular orientation. In some embodiments, endplate 26 may be disposed with end 18 for relative movement in orientations relative to axis X1, such as, for example, transverse, perpendicular and/or other angular orientations such as acute or obtuse, co-axial and/or may be offset or staggered. In some embodiments, endplate 26 may move relative to end 18 in alternate planes relative to a body, such as, for example, vertical, horizontal, diagonal, transverse, coronal and/or sagittal planes of a body. In some embodiments, endplate 26 may move relative to end 18 in a multi-axial configuration such that endplate 26 is rotatable to a selected angle through and within an angular range relative to axis X1 in a plurality of planes that lie in a cone configuration.

In some embodiments, stratum 102 includes a solid configuration that increases the strength of endplate 26. In some embodiments, stratum 102 includes an interconnected porous configuration, which facilitates bone ingrowth. In some embodiments, stratum 102 includes one or a plurality of layers. In some embodiments, stratum 102 includes one or a plurality of layers, which may include solid titanium, porous titanium, solid titanium-HA composite (porous titanium completely filled with HA) and/or porous titanium-coated with HA. In some embodiments, the cross-sectional geometry of endplate 26 may have various configurations, such as, for example, round, oval, oblong, triangular, polygonal having planar or arcuate side portions, irregular, uniform, non-uniform, consistent, variable, horseshoe shape, U-shape or kidney bean shape.

In some embodiments, stratum 86 and/or stratum 102 includes one or a plurality of openings configured for disposal of an agent such that the agent may vascularize through the openings. In some embodiments, the agent may be disposed, packed, coated or layered within, on or about the surfaces of stratum 86 and/or stratum 102. In some embodiments, the agent may include bone growth promoting material, such as, for example, bone graft to enhance fixation of the components and/or surfaces of stratum 86 and/or stratum 102 with vertebrae. In some embodiments, the agent may include one or a plurality of therapeutic agents and/or pharmacological agents for release, including sustained release, to treat, for example, pain, inflammation and degeneration.

Lock 106 includes a portion 108 and a portion 110. Portions 108, 110 are connected at a reduced diameter portion 112 that is tangibly connected to portion 110. In some embodiments, portion 110 is configured for a threaded engagement with end face 24. In some embodiments, portions 108, 110 are fabricated from a fracturing and/or frangible material such that manipulation of portion 108 relative to portion 110 can fracture and separate portion 108 from portion 110 at a predetermined force and/or torque limit, as described herein. In some embodiments, as force and/or torque is applied to portion 108 and resistance increases, for example, due to fixation of portion 110 with implant 12, as described herein, the predetermined torque and force limit is approached.

In some embodiments, portions 108, 110 can fracture and separate at a predetermined force or torque limit, which may be in a range of approximately 2 N-m to 8 N-m. In some embodiments, portions 108, 110 may have the same or alternate cross section configurations, may be fabricated from a homogenous material or heterogeneously fabricated from different materials, and/or alternately formed of a material having a greater degree, characteristic or attribute of plastic deformability, frangible property and/or break away quality to facilitate fracture and separation of portions 108, 110.

Figure 3:
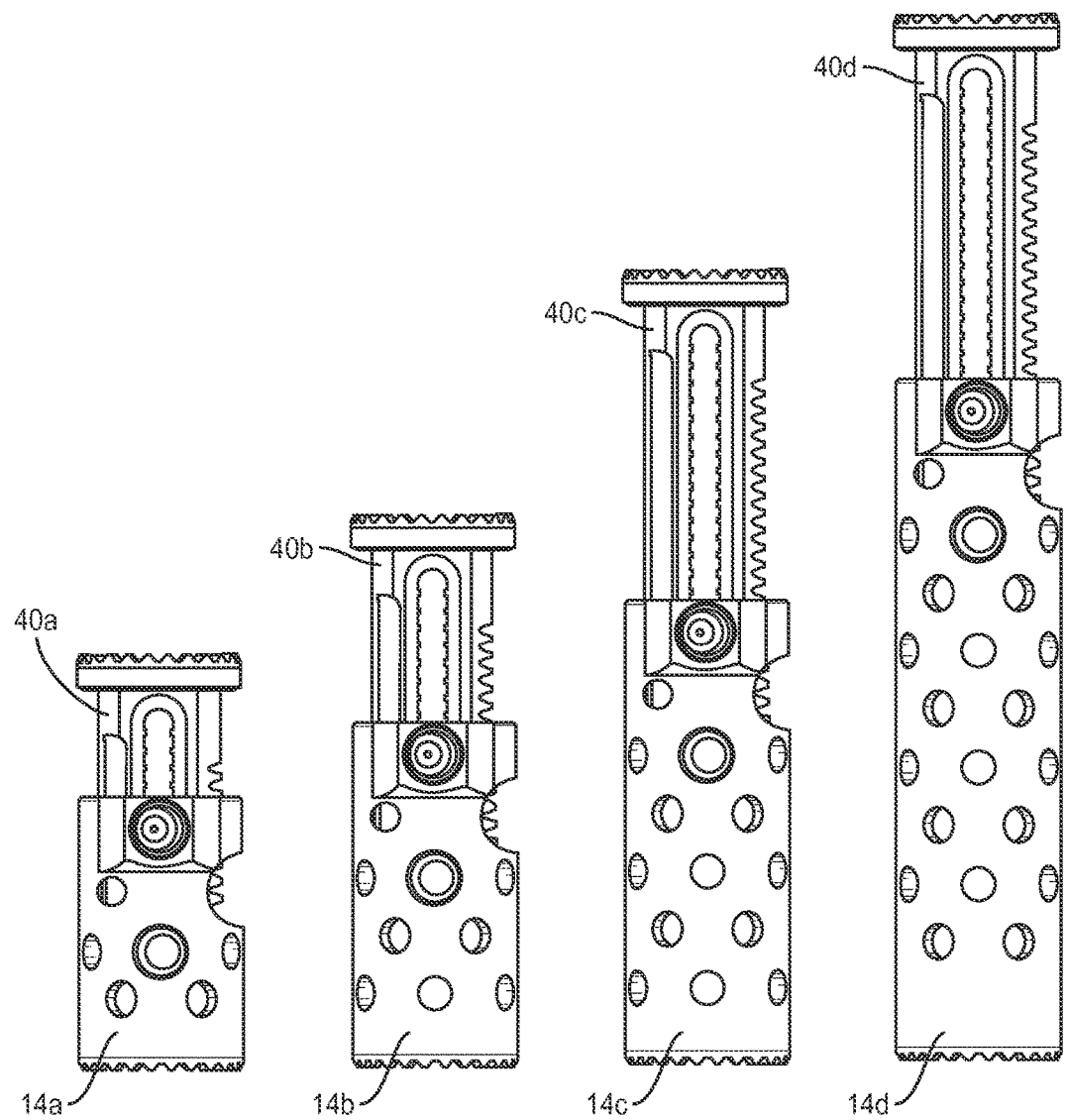
FIG. 3 is a side view of components of one embodiment of a surgical system in accordance with the principles of the present disclosure.
Figure 5:
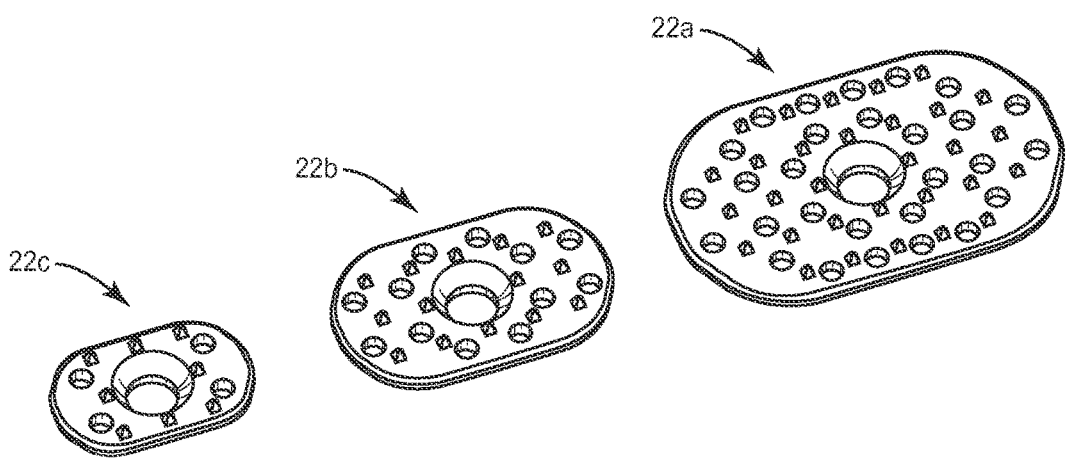
FIG. 5 is a perspective view of components of one embodiment of a surgical system in accordance with the principles of the present disclosure.

In some embodiments, spinal implant system 10 includes a kit. Components of the kit, as shown in FIGS. 3 and 5, include a plurality of bodies 14 and/or body 40 having various sizes, such as, for example, body 14a-14d and having various sizes, such as, for example, bodies 40a-40d. The plurality of bodies includes different sized widths and heights. In some embodiments, body 14 and/or body 40 are configured to be formed in various sizes/dimensions. In some embodiments, the range of dimensions of body 14 and/or body 40 include but are not limited to a height of 15.5 mm and a width of 23.5 mm, a height of 23 mm and a width of 32 mm, a height of 28 mm and a width of 44 mm, a height of 42 mm and a width of 58 mm, a height of 56 mm and a width of 72 mm, and a height of 70 mm and a width of 86 mm. In some embodiments, the kit includes a plurality of endplates 22, 26, such as, for example, endplates 22a-22c. Endplates 22, 26 are alternately sized and/or configured relative to one or more dimensions, as described herein, and configured to be interchangeable with body 14 and/or body 40.

In assembly, operation and use, spinal implant system 10 including spinal implant 12, similar to that described with regard to FIGS. 1-5, is employed with a surgical procedure, such as, for example, a lumbar corpectomy for treatment of a spine of a patient including vertebrae V, as shown in FIGS. 6-13. Spinal implant system 10 may also be employed with other surgical procedures, such as, for example, discectomy, laminectomy, fusion, laminotomy, laminectomy, nerve root retraction, foramenotomy, facetectomy, decompression, spinal nucleus or disc replacement and bone graft and implantable prosthetics including plates, rods, and bone engaging fasteners for securement of spinal implant 12.

Spinal implant system 10 is employed with a lumbar corpectomy including surgical arthrodesis, such as, for example, fusion to immobilize a joint for treatment of an applicable condition or injury of an affected section of a spinal column and adjacent areas within a body. For example, vertebrae V includes a vertebral level V1 and a vertebral level V2. Diseased and/or damaged vertebrae and intervertebral discs are disposed between vertebrae V1 and V2. In some embodiments, spinal implant system 10 is configured for insertion with a vertebral space to space apart articular joint surfaces, provide support and maximize stabilization of vertebrae V.

In use, to treat the affected section of vertebrae V, a medical practitioner obtains access to a surgical site including vertebrae V in any appropriate manner, such as through incision and retraction of tissues. In some embodiments, spinal implant system 10 may be used in any existing surgical method or technique including open surgery, mini-open surgery, minimally invasive surgery and percutaneous surgical implantation, whereby vertebrae V is accessed through a mini-incision, or sleeve that provides a protected passageway to the area. Once access to the surgical site is obtained, a corpectomy is performed for treating the spine disorder. The diseased and/or damaged portions of vertebrae V, and diseased and/or damaged intervertebral discs are removed to create a vertebral space S.

A preparation instrument (not shown) is employed to remove disc tissue, fluids, adjacent tissues and/or bone, and scrape and/or remove tissue from endplate surface E1 of vertebral level V1 and/or endplate surface E2 of vertebral level V2. Spinal implant 12 is provided with at least one agent, similar to those described herein and as described above, to promote bone growth and fusion to treat the affected section of vertebrae V.

Figure 6:
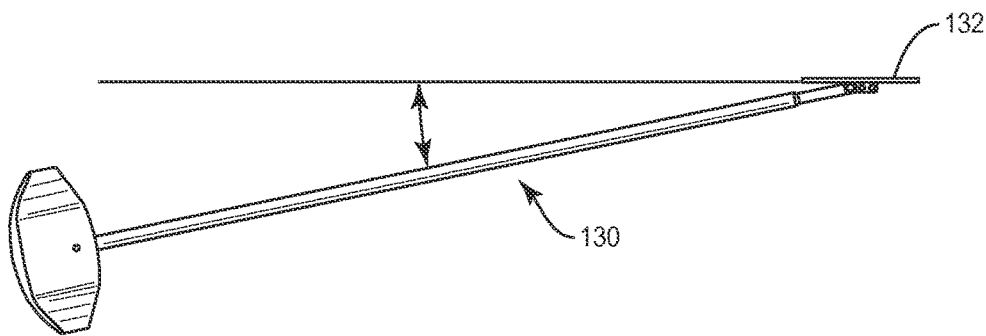
FIG. 6 is a side view of components of one embodiment of a surgical system in accordance with the principles of the present disclosure.
Figure 7:
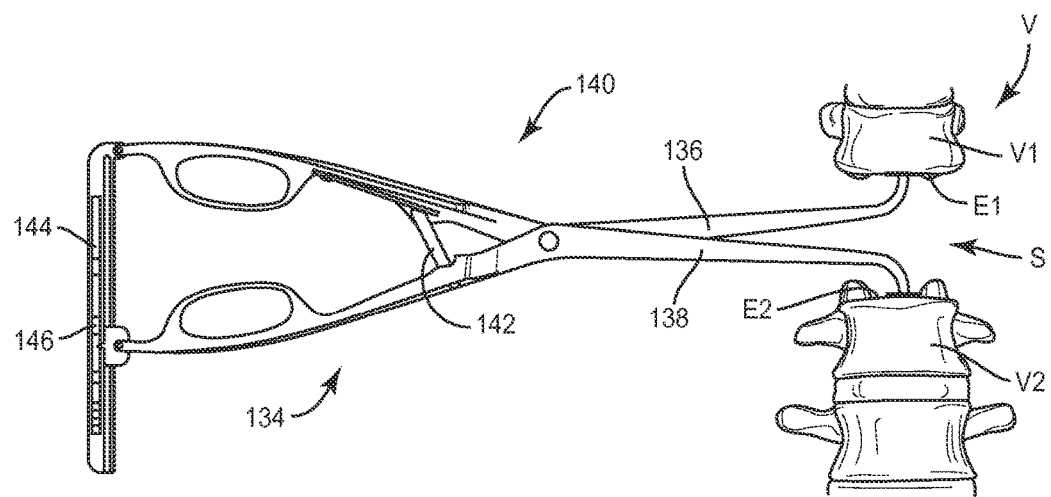
FIG. 7 is a side view of components of one embodiment of a surgical system in accordance with the principles of the present disclosure disposed with vertebrae.

In some embodiments, a surgical instrument 130 including, such as, for example, a template 132, as shown in FIG. 6, is inserted into vertebral space S to determine a size for endplate 22 and/or endplate 26, as described herein. In some embodiments, a surgical instrument, such as, for example, a sizer 134 is utilized to determine an implant height, such as, for example, a height for body 14 and/or body 40. Sizer 134 includes an arm 136 configured to engage endplate E1 and an arm 138 configured to engage endplate E2. A handle 140 is configured to manipulate arms 136, 138 to facilitate determination of the height of the implant. Handle 140 includes a lock, such as, for example, a lever 142 configured to fix arm 136 relative to arm 138 to facilitate measurement of the height of vertebral space S. In some embodiments, handle 140 includes a plate 144 that includes indicia 146 to indicate the height of vertebral space S.

In some embodiments, spinal implant system 10 includes a spinal implant kit having a plurality of alternate endplates 22, 26 that are interchangeable with a plurality of bodies 14, 30, as described herein. Endplates 22, 26 and bodies 14, 40 are selected for assembly of a spinal implant 12 with a body 14/body 40 size and/or configuration, endplate 22, 26 size and/or configuration, predetermined footprint size and/or expansion capability.

Figure 13:
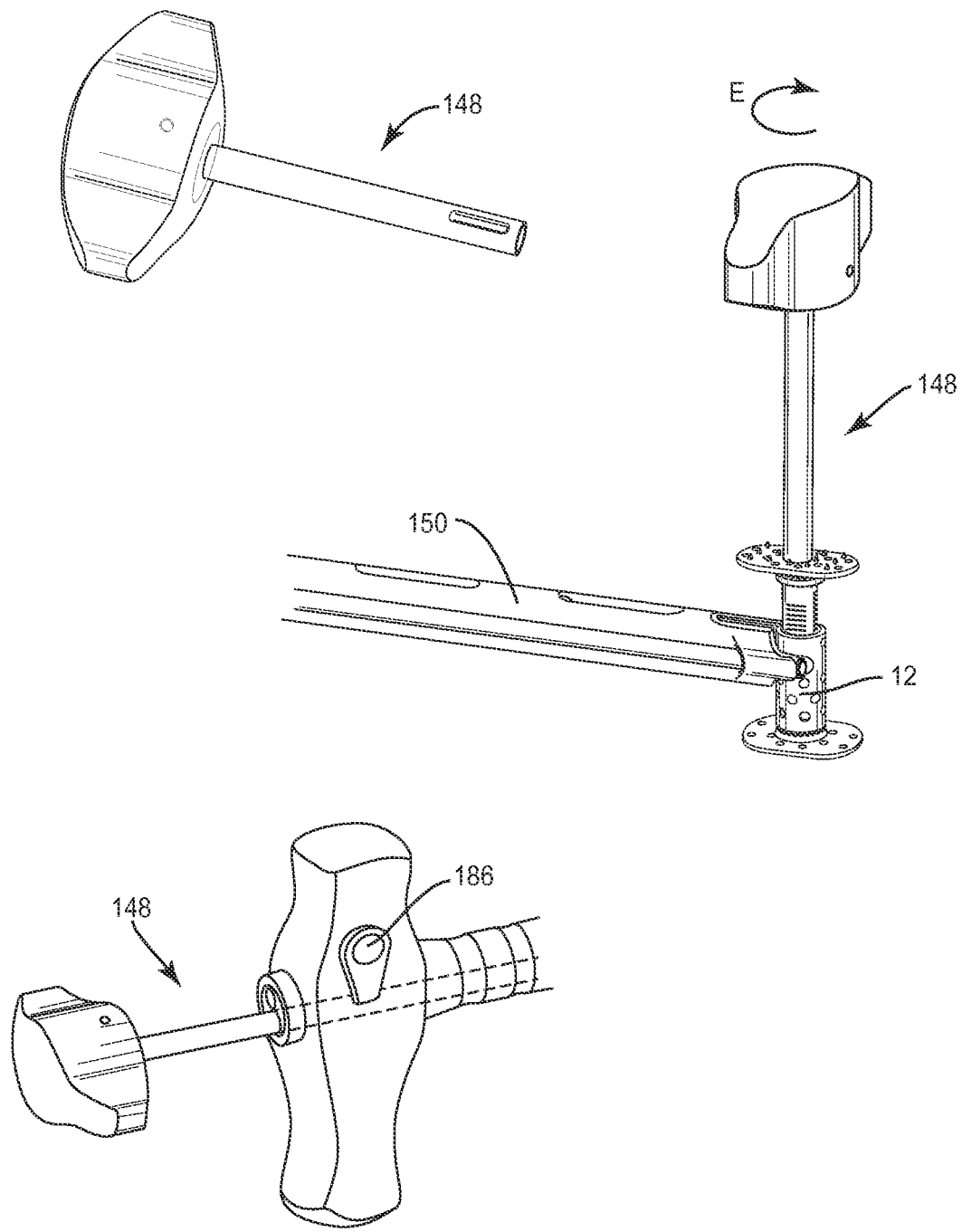
FIG. 13 illustrates perspective views of components of one embodiment of a surgical system in accordance with the principles of the present disclosure.

Endplates 22, 26 are attached to bodies 14, 40, as described herein, with a surgical instrument, such as, for example, a short nut driver 148, as shown in FIG. 13. Driver 148 is utilized for a dual purpose. Driver 148 is configured to attach locks 90, 106 with bodies 14, 40 and endplates 22, 26. Driver 148 is rotated to engage locks 90, 106 with openings 88, 104. Driver 148 is rotated, as shown by arrow E in FIG. 13, to a predetermined force and/or torque limit, to cause portions 108, 92 to break off.

Figure 8:
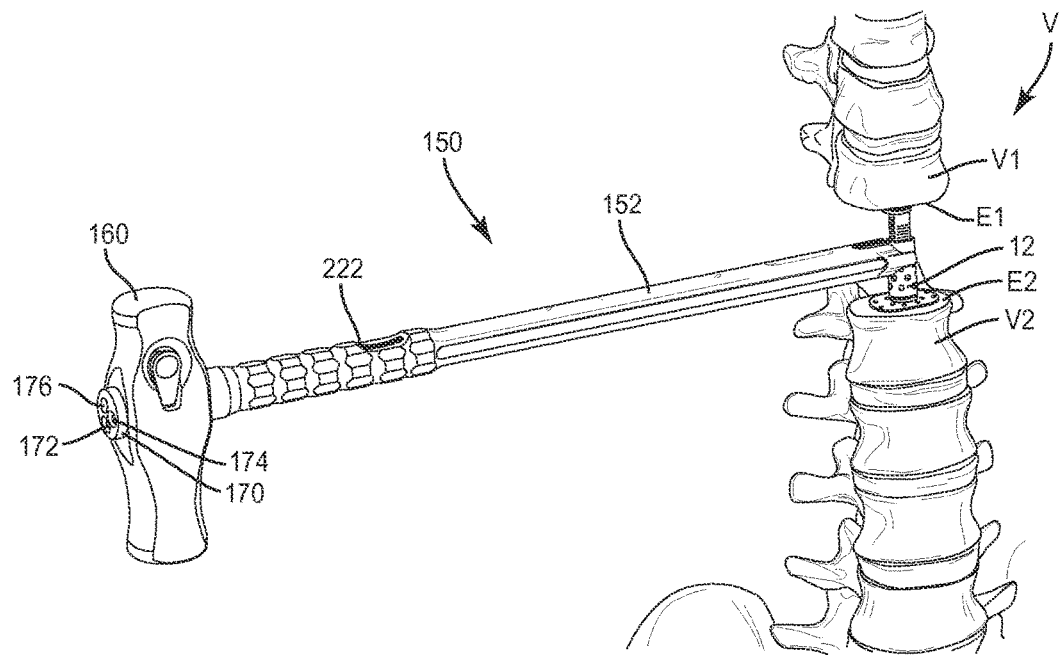
FIG. 8 is a perspective view of components of one embodiment of a surgical system in accordance with the principles of the present disclosure disposed with vertebrae.
Figure 9:
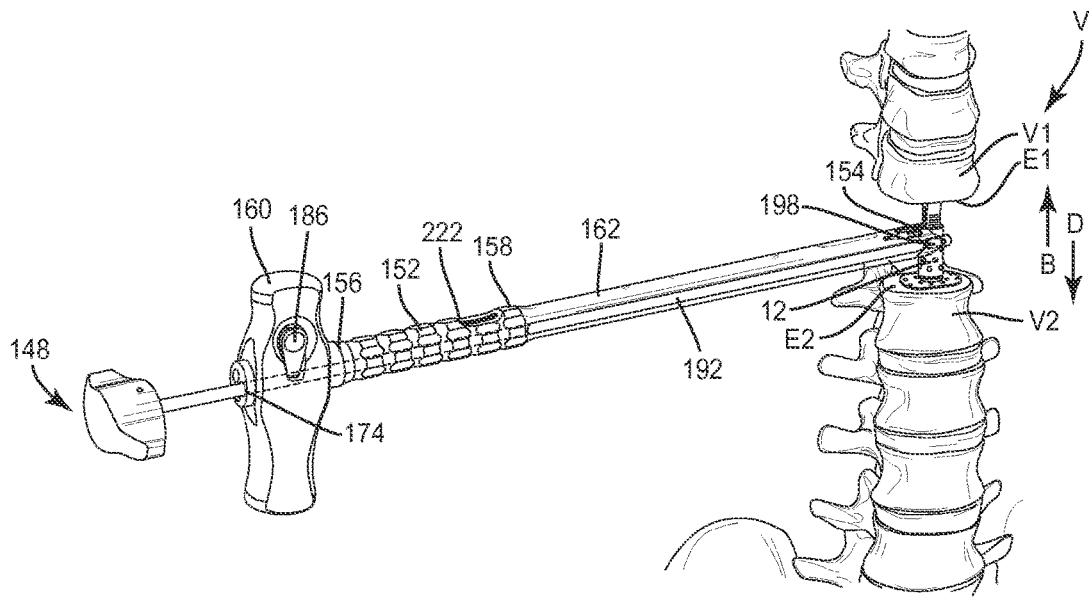
FIG. 9 is a perspective view of components of one embodiment of a surgical system in accordance with the principles of the present disclosure disposed with vertebrae.
Figure 10:
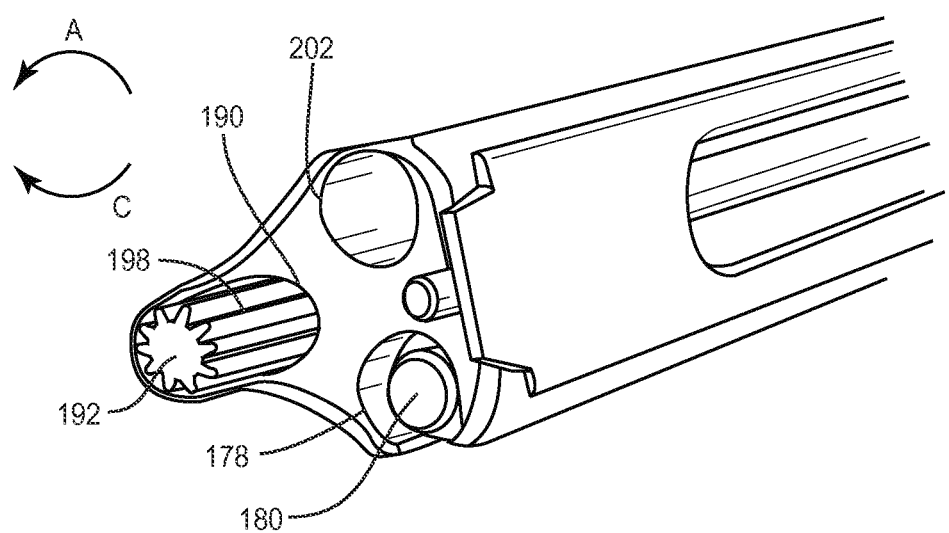
FIG. 10 is an enlarged, break away end view of components of the surgical system shown in FIG. 9.
Figure 11:
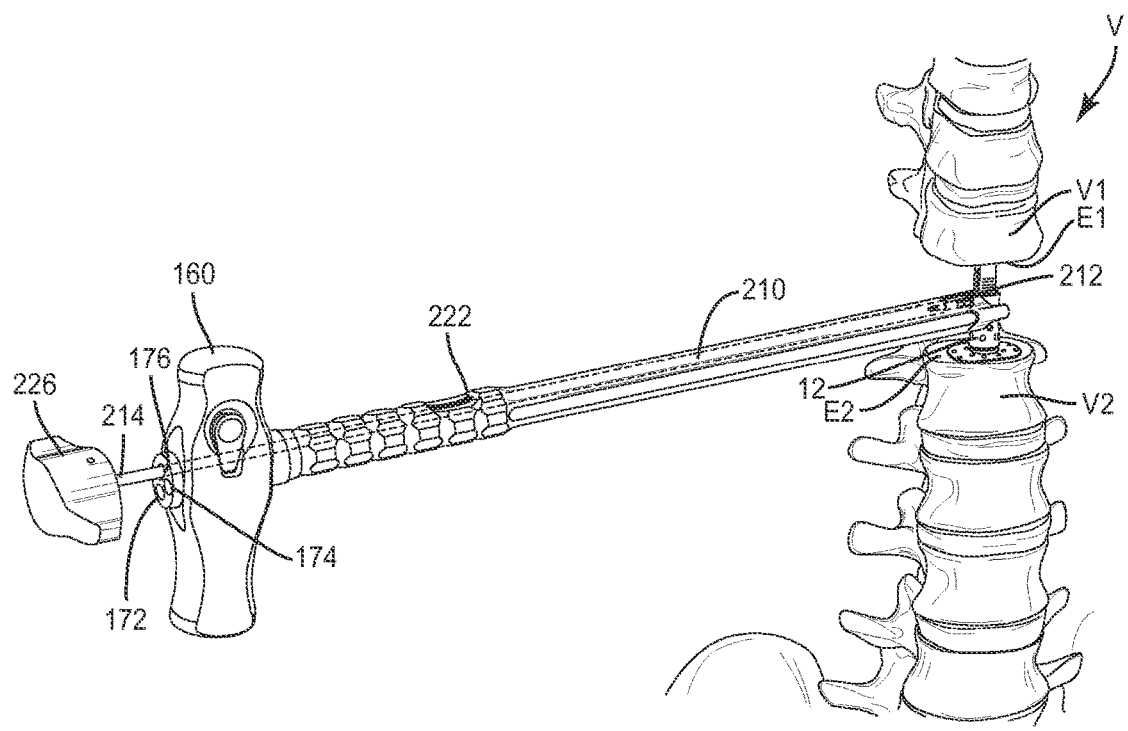
FIG. 11 is a perspective view of components of one embodiment of a surgical system in accordance with the principles of the present disclosure disposed with vertebrae.
Figure 12:
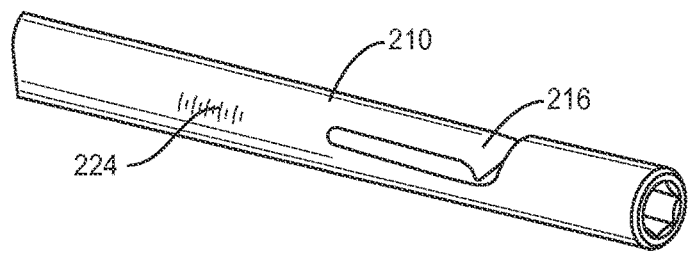
FIG. 12 is an enlarged, break away view of components of the surgical system shown in FIG. 11.

Inserter 150 is configured for attachment to spinal implant 12 and configured to facilitate insertion and expansion of spinal implant 12, as shown in FIGS. 8-10. Inserter 150 includes a body 152 that extends between an end 154 and an end 156. Body 152 includes a sleeve 158 and a handle 160. Sleeve 158 includes a surface, such as, for example, a tubular housing 162. Handle 160 includes a surface 170. Surface 170 defines an opening 172, an opening 174 and an opening 176.

Housing 162 defines a passageway 178 configured for disposal of a surgical instrument, such as, for example, a shaft 180. Passageway 178 is in communication with opening 172 such that shaft 180 extends through passageway 178. A distal end of shaft 180 is configured for engagement with a threaded opening 50 of body 14 to releasably fix spinal implant 12 with inserter 150. In some embodiments, shaft 180 is threadingly engaged with body 40. In some embodiments, shaft 180 may include engaging structures, such as, for example, barbs, tongs, raised elements and/or spikes to facilitate engagement with spinal implant 12. A proximal end of shaft 180 is configured for engagement with driver 148 to facilitate engagement of shaft 180 with spinal implant 12.

Housing 162 defines a passageway 190 configured for disposal of a surgical instrument, such as, for example, a driver 192. Passageway 190 is in communication with opening 174. Driver 192 is configured for insertion through opening 174 into passageway 190. Driver 192 is configured for expanding and contracting body 40 relative to body 14. A distal end of driver 192 includes a pinion gear portion 198 configured for engagement with teeth 62 of rack 60. Pinion gear portion 198 extends a distance past end 154 to facilitate engagement with spinal implant 12. A proximal end of driver 192 extends through handle 160 and is configured for engagement with driver 148 that is connected to and configured to rotate driver 192 such that pinion gear portion 198 engages spinal implant 12 to expand, contract, collapse and/or extend spinal implant 12. As such, driver 148 is configured to provide a tactile feel of distraction forces during expansion. In some embodiments, driver 192 is engageable with an actuator, such as, for example, a quick release button 186. Button 186 is engageable with driver 192 to provisionally maintain distraction of vertebrae V, as described herein, or to release the distraction.

Housing 162 defines a passageway 202 configured for moveable disposal of at least a portion of a surgical instrument, such as, for example, a driver 210, as described herein. Passageway 202 is in communication with opening 176 such that driver 210 can be inserted through opening 176 into passageway 202. Passageway 202 guides driver 210 to spinal implant 12. Driver 210 includes an engagement portion, such as, for example, a flange 216. Flange 216 is configured to engage lock 70, as described herein, to releasably fix lock 70 with driver 210. In some embodiments, flange 216 includes configurations, such as, for example, triangular, square, polygonal, hexalobular, star or torx. Body 152 includes an opening 222 for viewing visual indicia 224 disposed on driver 210. Visual indicia 224 is configured to indicate confirmation of fixation of lock 70 with spinal implant 12. Driver 210 includes a rotatable handle 226 configured to rotate driver 210 such that lock 70 locks spinal implant 12 in a fixed configuration. In some embodiments, handle 226 is a T-handle.

Spinal implant 12 is disposed in a first orientation, such that body 14 and body 40 are disposed in a concentric configuration with longitudinal axis X1 and disposed in a telescopic arrangement for delivery and implantation adjacent vertebral space S. Bodies 14, 40 are seated concentrically such that substantially all of inner body 40 is disposed within outer body 14 in a nested configuration. Driver 148 actuates shaft 180, which is engaged with body 14 to releasably fix spinal implant 12 with inserter 150.

Spinal implant 12 is delivered to the surgical site adjacent vertebrae V via inserter 150. Inserter 150 delivers spinal implant 12 into the prepared vertebral space S, between vertebral level V1 and vertebral level V2. Driver 192 is inserted through opening 174 into passageway 190. Pinion gear portion 198 engages teeth 62 of rack 60. Driver 148 is utilized to actuate driver 192 to expand and contract bodies 14, 40. Driver 192 is rotated, in a direction shown by arrow A in FIG. 10. As driver 192 is rotated, pinion gear portion 198 engages teeth 62 of rack 60 causing body 40 to axially translate, in the direction shown by arrow B in FIG. 9, relative to body 14 to facilitate expansion of spinal implant 12. Driver 192 can be rotated in an opposite direction, as shown by arrow C in FIG. 10, to collapse spinal implant 12. As driver 192 is rotated in the opposite direction, pinion gear portion 198 engages teeth 62 of rack 60 causing body 40 to axially translate, in a direction shown by arrow D in FIG. 9, relative to body 14 to facilitate contraction of body 40 relative to body 14. In some embodiments, inserter 150 is engageable with bodies 14, 40 to provisionally fix bodies 14, 40 in a selected orientation. In some embodiments, expansion of spinal implant 12 is provisionally maintained via button 186 while lock screw 70 is inserted to permanently secure expansion of spinal implant 12.

Spinal implant 12 engages and spaces apart opposing endplate surfaces E1, E2 and is secured within vertebral space S to stabilize and immobilize portions of vertebrae V in connection with bone growth for fusion and fixation of vertebral levels V1, V2. Fixation of spinal implant 12 with endplate surfaces E1, E2 may be facilitated by the resistance provided by the joint space and/or engagement with endplate surfaces E1, E2.

Driver 210 is inserted through opening 176 and into passageway 202 to engage lock 70. Handle 226 is manipulated to fix lock 70, as described herein, with spinal implant 12 to prevent body 40 from axially translating relative to body 14 to fix implant 12 in a selected expanded and/or contracted orientation.

In some embodiments, spinal implant 12 may engage only one endplate. In some embodiments, agent(s), as described herein, may be applied to areas of the surgical site to promote bone growth. Components of spinal implant system 10 including spinal implant 12 can be delivered or implanted as a pre-assembled device or can be assembled in situ. Components of spinal implant system 10 including spinal implant 12 may be completely or partially revised, removed or replaced in situ. In some embodiments, one or all of the components of spinal implant system 10 can be delivered to the surgical site via mechanical manipulation and/or a free hand technique.

In one embodiment, spinal implant 12 may include fastening elements, which may include a locking structure, configured for fixation with vertebral levels V1, V2 to secure joint surfaces and provide complementary stabilization and immobilization to a vertebral region. In some embodiments, the locking structure may include fastening elements such as, for example, rods, plates, dips, hooks, adhesives and/or flanges. In some embodiments, spinal implant system 10 can be used with screws to enhance fixation. In some embodiments, spinal implant system 10 and any screws and attachments may be coated with an agent, similar to those described herein, for enhanced bony fixation to a treated area. The components of spinal implant system 10 can be made of radiolucent materials such as polymers. Radiomarkers may be included for identification under x-ray, fluoroscopy, CT or other imaging techniques.

In one embodiment, spinal implant system 10 includes a plurality of spinal implants 12. In some embodiments, employing a plurality of spinal implants 12 can optimize the amount vertebral space S can be spaced apart such that the joint spacing dimension can be preselected. The plurality of spinal implants 12 can be oriented in a side by side engagement, spaced apart and/or staggered.

In some embodiments, use of microsurgical and image guided technologies may be employed to access, view and repair spinal deterioration or damage, with the aid of spinal implant system 10. Upon completion of the procedure, the non-implanted components, surgical instruments and assemblies of spinal implant system 10 are removed and the incision is closed.

Figure 14:
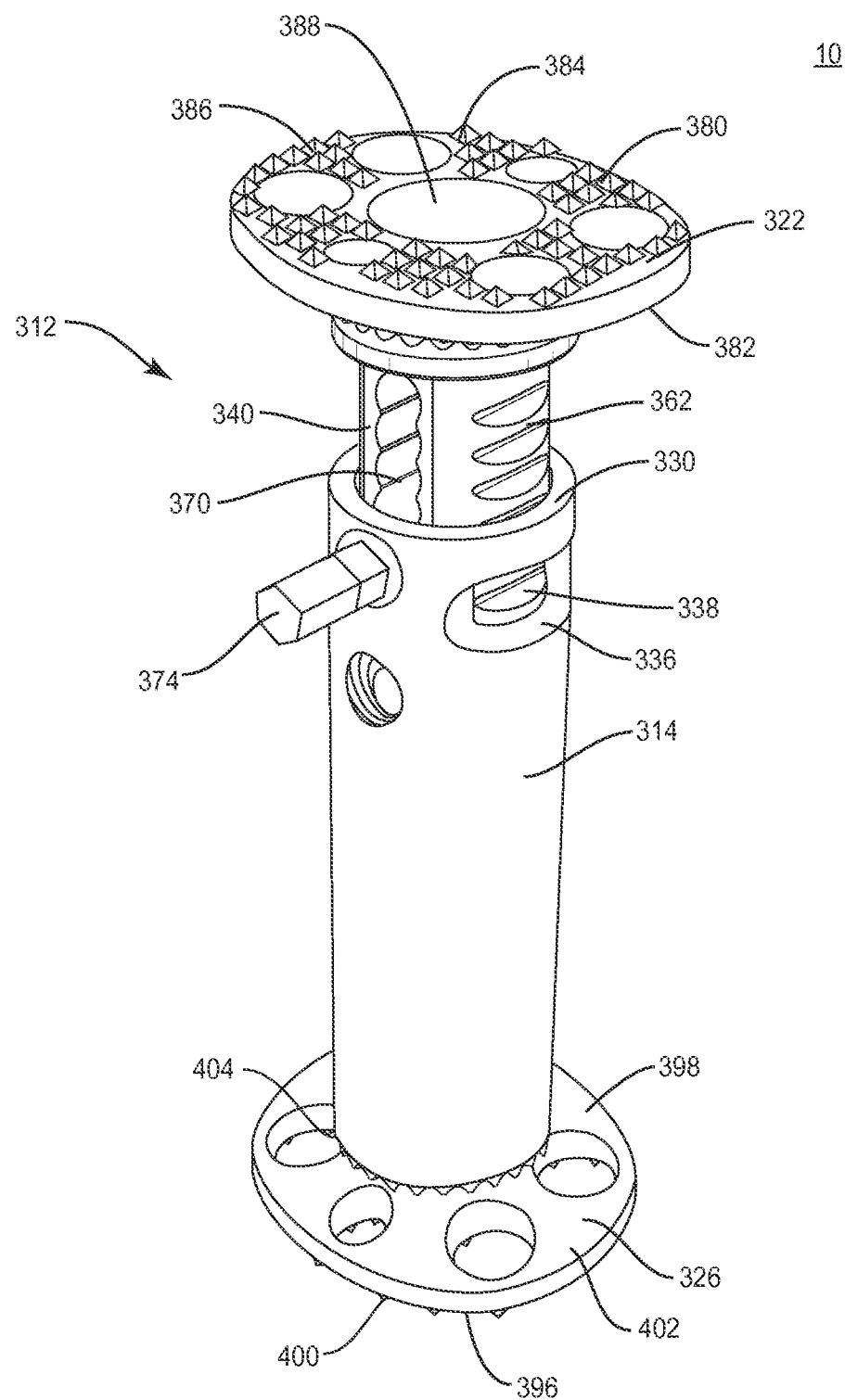
FIG. 14 is a perspective view of components of one embodiment of a surgical system in accordance with the principles of the present disclosure.
Figure 15:
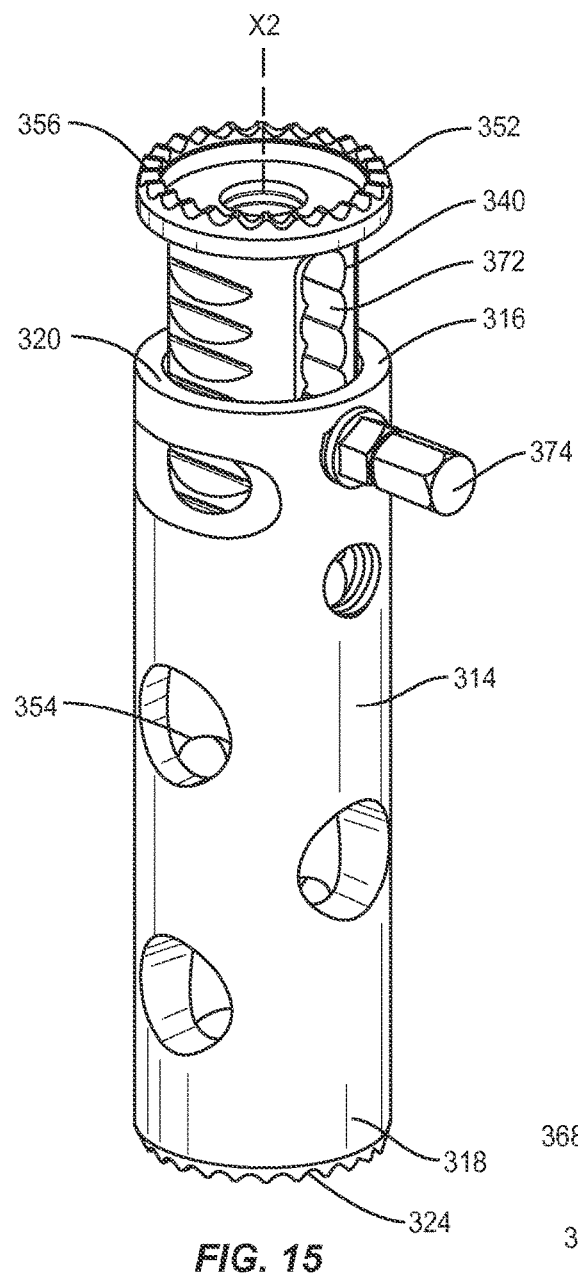
FIG. 15 is a perspective view of components of one embodiment of a surgical system in accordance with the principles of the present disclosure.
Figure 16:
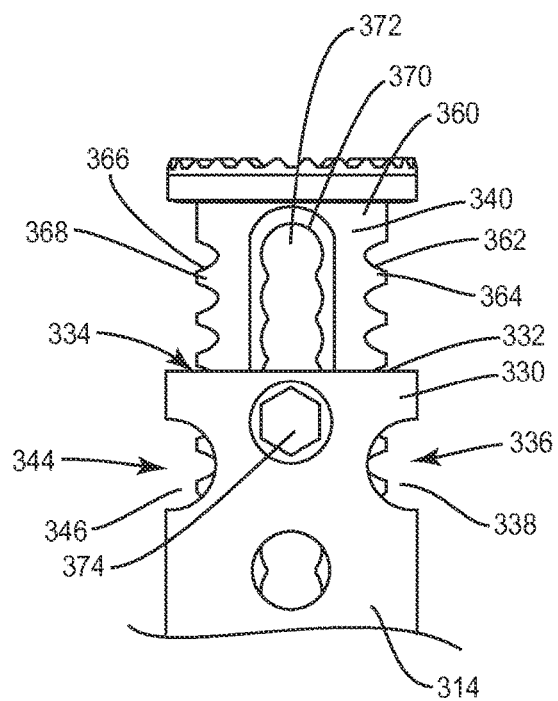
FIG. 16 is a side view of components of one embodiment of a surgical system in accordance with the principles of the present disclosure.

In one embodiment, as shown in FIGS. 14-16, spinal implant system 10, similar to the systems and methods described with regard to FIGS. 1-13, includes a spinal implant 312, similar to the spinal implants described herein. Spinal implant 312 includes an outer body 314 having a tubular configuration. Body 314 extends in a linear configuration and defines a longitudinal axis X2. Body 314 extends between an end 316 and an end 318. End 316 defines an end face 320 configured to engage vertebral tissue and/or an endplate 322, as described herein. End 318 defines an end face 324 that is configured to engage vertebral tissue and/or an endplate 326, as described herein.

Body 314 includes a tubular wall 330. Wall 330 includes an inner surface 332 that defines an axial cavity 334 extending between ends 316, 318. Wall 330 includes an inwardly oriented surface that defines a lateral cavity, such as, for example, a side window 336. Window 336 includes an aperture, such as, for example, opening 338. Opening 338 is configured for disposal of a surgical instrument utilized to facilitate expansion of body 314 and an inner body 340 of spinal implant 312, as described herein. Opening 338 has a circular aperture configuration and is oriented for disposal of a surgical instrument, such as, for example, an inserter 450, as described herein, configured for engagement with gear teeth of body 340, as described herein. Opening 338 is oriented substantially transverse, such as, for example, perpendicular to axis X2.

Wall 330 includes an inwardly oriented surface that defines a lateral cavity, such as, for example, a side window 344. Window 344 is disposed contralateral to window 336, as shown in FIG. 16. Window 344 includes an aperture, such as, for example, opening 346. Opening 346 is configured for disposal of a surgical instrument utilized to facilitate expansion of body 314 and an inner body 340 of spinal implant 312, as described herein. Opening 346 has a circular aperture configuration and is oriented for disposal of a surgical instrument, such as, for example, an inserter 450, as described herein, configured for engagement with gear teeth of body 340, as described herein. Opening 346 is oriented substantially transverse, such as, for example, perpendicular to axis X2.

In some embodiments, openings 338, 346 may be variously oriented relative to axis X2, such as, for example, parallel or angled, which may include acute and obtuse orientations. In some embodiments, openings 338, 346 may be variously configured, such as, for example, oval, oblong, triangular, polygonal having planar or arcuate side portions, irregular, uniform, non-uniform, consistent, variable, horseshoe shape, U-shape or kidney bean shape.

Body 340 has a tubular configuration and is oriented for disposal within axial cavity 334. Body 340 extends in a linear configuration relative to axis X2. In some embodiments, body 340 may extend in alternate configurations, such as, for example, arcuate, offset, staggered and/or angled portions, which may include acute, perpendicular and obtuse.

Body 340 extends between an end 352 and an end 354. End 354 defines an end face 356 configured to engage vertebral tissue and/or endplate 322, as described herein. In some embodiments, end 352 and/or end 354 can include a surface that may be rough, textured, porous, semi-porous, dimpled and/or polished. In some embodiments, both or only one of ends 352, 354 may engage tissue to provide treatment, as described herein.

Body 340 includes a wall, such as, for example, a tubular wall 356. Wall 356 includes an inner surface 358 that defines an axial cavity 360 extending between ends 353, 354. In some embodiments, wall 356 includes a cylindrical cross-section. Body 340 is configured for disposal with cavity 334 such that walls 330, 356 are concentric with axis X2.

Wall 356 includes a surface 360. Surface 360 includes a gear rack 362 having a plurality of teeth 364 that are disposed therealong. Teeth 364 are disposed in a linear, serial configuration along surface 360 in an offset configuration relative to axis X2. The offset configuration of teeth 364 cause teeth 364 to extend into opening 338 to facilitate engagement with a pinion gear 528 of inserter 450 through opening 338, as described herein. Engagement of inserter 450 with teeth 364 axially translates body 340 relative to body 314 between a contracted configuration and an expanded configuration for disposal in a selected orientation, as described herein.

Surface 360 includes a gear rack 366 having a plurality of teeth 368 that are disposed therealong. Teeth 368 are disposed in a linear, serial configuration along surface 360 in an offset configuration relative to axis X2 and contralateral to teeth 364. The offset configuration of teeth 368 cause teeth 368 to extend into opening 346 to facilitate engagement with a pinion gear 528 of inserter 450 through opening 346, as described herein. Engagement of inserter 450 with teeth 368 axially translates body 340 relative to body 314 between a contracted configuration and an expanded configuration for disposal in a selected orientation, as described herein Wall 356 includes a surface 370. Surface 370 defines an opening, such as, for example, an axial slot 372. Slot 372 is disposed along axis X2. Slot 372 is configured for engagement with a lock 374, similar to lock 70, as described herein.

Endplate 322, similar to endplate 22, is configured for engagement with end 352 of body 340. Endplate 322 extends between a vertebral engaging surface 380 and a surface 382. Surface 380 includes one or a plurality of tissue penetrating members, such as, for example, teeth 384. In one embodiment, one or more teeth 384 may have various configurations, for example, round, oval, rectangular, polygonal, irregular, tapered, offset, staggered, uniform and non-uniform. In some embodiments, surface 380 may be rough, textured, porous, semi-porous, dimpled, knurled, grooved and/or polished to facilitate engagement with tissue. In some embodiments, the vertebral tissue may include intervertebral tissue, endplate surfaces and/or cortical bone.

Endplate 322 includes a stratum 386. Stratum 386 includes at least one mating element, such as, for example, an opening 388 configured for engagement with a lock (not shown), similar to lock 90, as described herein, configured for mating engagement with an opening disposed with end face 356, as described herein. In some embodiments, endplate 322 is rotatable about and relative to axis X2 and is moveable in a plurality of angular orientations relative to axis X2.

Endplate 326 is configured for engagement with end 318 of body 314. Endplate 326 extends between a vertebral engaging surface 396 and a surface 398. Surface 396 includes one or a plurality of tissue penetrating members, such as, for example, teeth 400. Endplate 326 includes a stratum 402. Stratum 402 includes at least one mating element, such as, for example, an opening 404 configured for engagement with a lock (not shown), similar to lock 106, as described herein, configured for mating engagement with an opening disposed with end face 324, as described herein. In some embodiments, endplate 326 is rotatable about and relative to axis X2 and is moveable in a plurality of angular orientations relative to axis X2.

Figure 17:
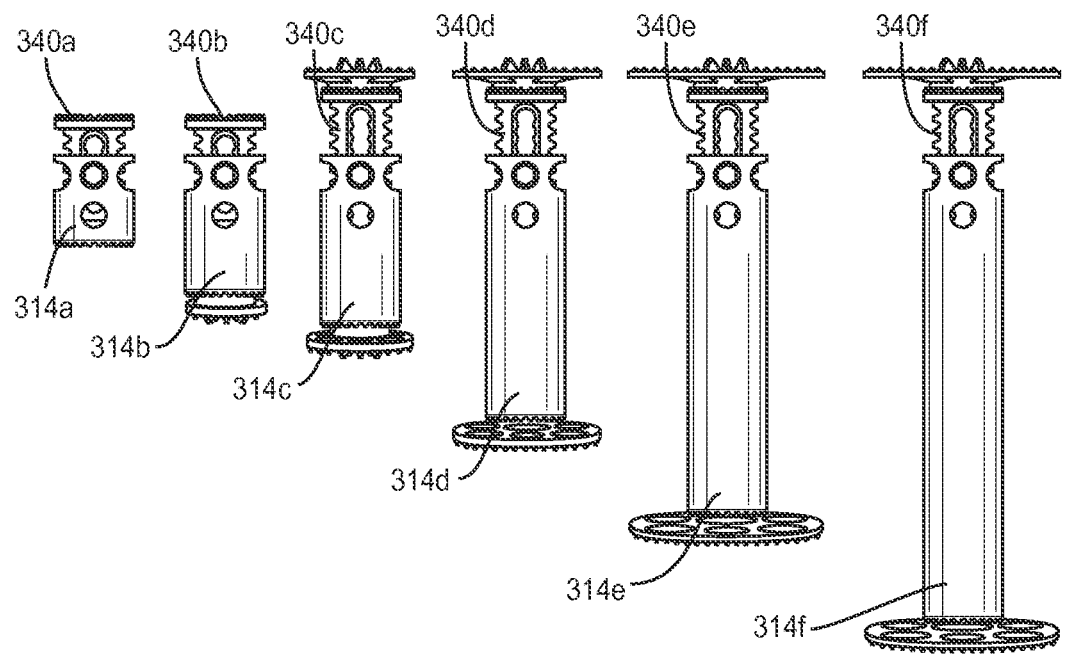
FIG. 17 is a perspective view of components of one embodiment of a surgical system in accordance with the principles of the present disclosure.
Figure 17:
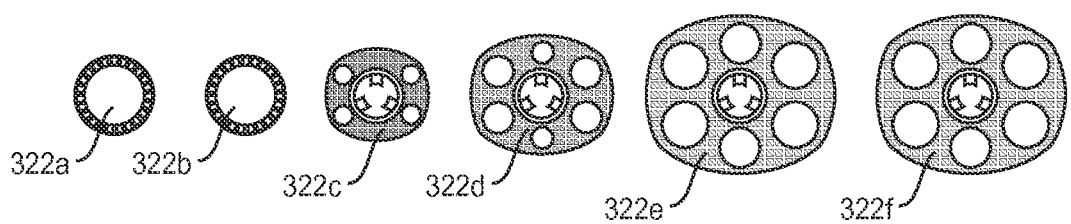
Figure 18:
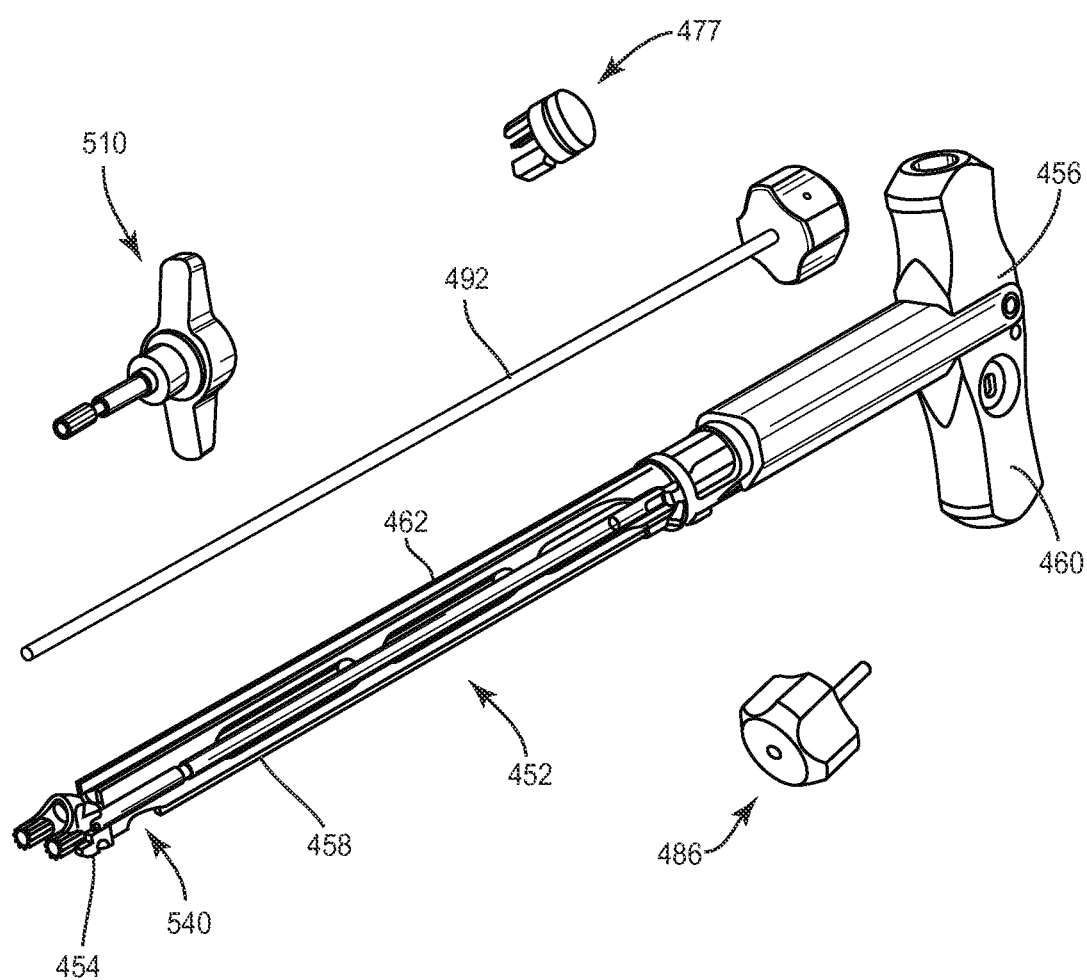
FIG. 18 illustrates perspective views of components of one embodiment of a surgical system in accordance with the principles of the present disclosure.
Figure 19:
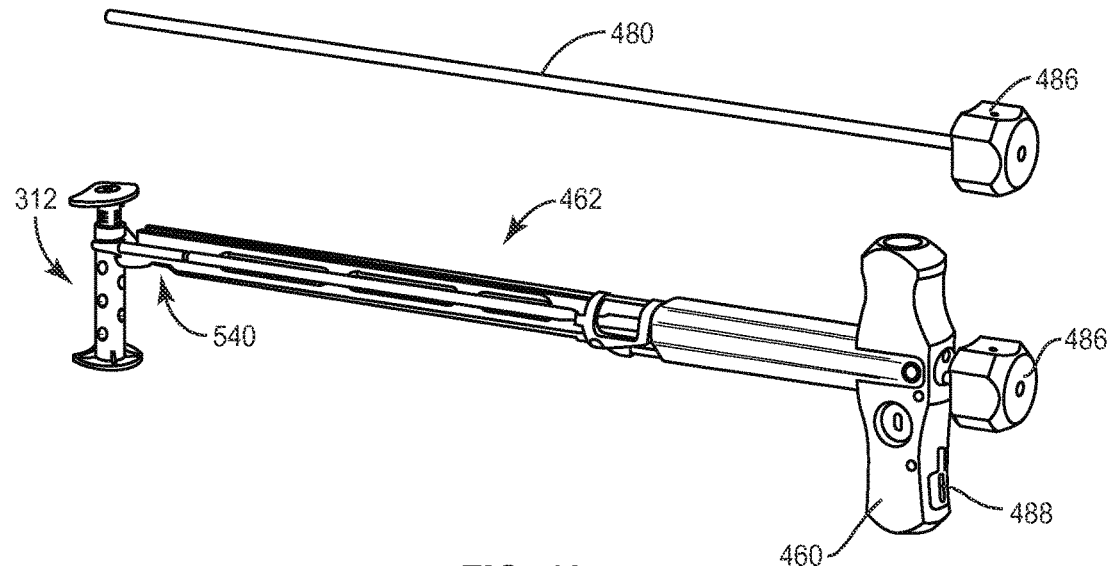
FIG. 19 is a perspective view of components of one embodiment of a surgical system in accordance with the principles of the present disclosure.

In some embodiments, spinal implant system 10, similar to the systems and methods described herein, includes a kit. Components of the kit, as shown in FIG. 17, include a plurality of bodies 314 and/or body 340 having various sizes, such as, for example, body 314a-314f, and having various sizes, such as, for example, body 340a-340f. The kit includes a plurality of endplates 322, 326, such as, for example, endplates 322a-322f. Endplates 322, 326 are alternately sized and/or configured relative to one or more dimensions, as described herein, and configured to be interchangeable with body 314 and/or body 340.

In some embodiments, as shown in FIGS. 18-24, spinal implant system 10, similar to the systems and methods described herein, includes inserter 450 configured for attachment to a spinal implant, such as, for example, spinal implant 312 described herein and to facilitate a variable angled insertion and expansion of spinal implant 312. Inserter 450 includes a body 452 that defines an axis A1 and extends between an end 454 and an end 456. Body 452 includes a sleeve 458 and a handle 460. Sleeve 458 includes a surface, such as, for example, a tubular housing 462. Handle 460 includes a surface 472. Surface 472 defines an opening 474 and an opening 476. In some embodiments, surface 472 includes an insert, such as, for example, an impaction head 477.

Housing 462 defines a passageway 478 configured for disposal of a shaft 480. Passageway 478 is in communication with opening 476 such that shaft 480 extends through passageway 478. A distal end of shaft 480 is configured for engagement with body 314 to releasably fix spinal implant 312 with inserter 450. In some embodiments, shaft 480 is threadingly engaged with body 340. In some embodiments, shaft 480 may include engaging structures, such as, for example, barbs, tongs, raised elements and/or spikes to facilitate engagement with spinal implant 312. A proximal end of shaft 480 is configured for engagement with a surgical instrument, such as, for example, a driver 486 to facilitate engagement of shaft 480 with spinal implant 312.

Housing 462 defines a passageway 490 configured for disposal of a surgical instrument, such as, for example, a driver 492. Passageway 490 is in communication with opening 474 such that driver 492 is inserted through opening 474 into passageway 490. Passageway 490 guides driver 492 to spinal implant 312. Driver 492 is configured to engage lock 374, as described herein, to releasably fix lock 374 with spinal implant 312. Driver 492 includes a handle 498 configured to facilitate manipulation of driver 492.

Housing 462 defines a passageway 500. Passageway 500 is configured for disposal of a driver 502. Driver 502 is configured for expanding and contracting body 340 relative to body 314. A distal end of driver 502 includes a pinion gear portion 508 configured for engagement with teeth 364 of rack 362. Pinion gear portion 508 extends a distance past end 454 to facilitate engagement with spinal implant 312. Driver 502 extends into handle 460 for engagement with a spur gear key 510, as described herein. Pinion gear portion 508 is pivotable to facilitate angulation of implant 312 during insertion, as described herein.

Housing 462 defines a passageway 520. Passageway 520 is disposed contralateral to passageway 500. Passageway 520 is configured for disposal of a driver 522. Driver 522 is configured for expanding and contracting body 340 relative to body 314 in conjunction with driver 502 for a dual gripping configuration. A distal end of driver 522 includes a pinion gear portion 528 configured for engagement with teeth 368 of rack 366. Pinion gear portion 528 extends a distance past end 454 to facilitate engagement with spinal implant 312. A proximal end of driver 522 extends into handle 460 for engagement with spur gear key 510, as described herein. In some embodiments, driver 502 is symmetrical with driver 522. Pinion gear portion 528 is pivotable to facilitate angulation of spinal implant 312 during insertion, as described herein. In some embodiments, an actuator, such as, for example, a quick release button 488 is engageable with driver 502 and/or driver 522 to maintain distraction of vertebrae V, as described herein, or to release the distraction.

Spur gear key 510 is engageable with a gear mechanism (not shown) attached with drivers 502, 522. Spur gear key 510 is inserted into one of openings 530 disposed with handle 460 to engage the drive mechanism to facilitate rotation of gear portions 508, 528 to expand and/or contract spinal implant 312. Openings 530 are disposed on handle 460 at various locations to facilitate expansion and contraction of spinal implant 312. Handle 460 includes indicia 532 configured to indicate graduations of a height of spinal implant 312 during expansion. Drivers 502, 522 are disposed within intermediate part 534 connected to a linkage 540, described herein, and part 534 is configured for slidable engagement with drivers 502, 522.

Figure 20:
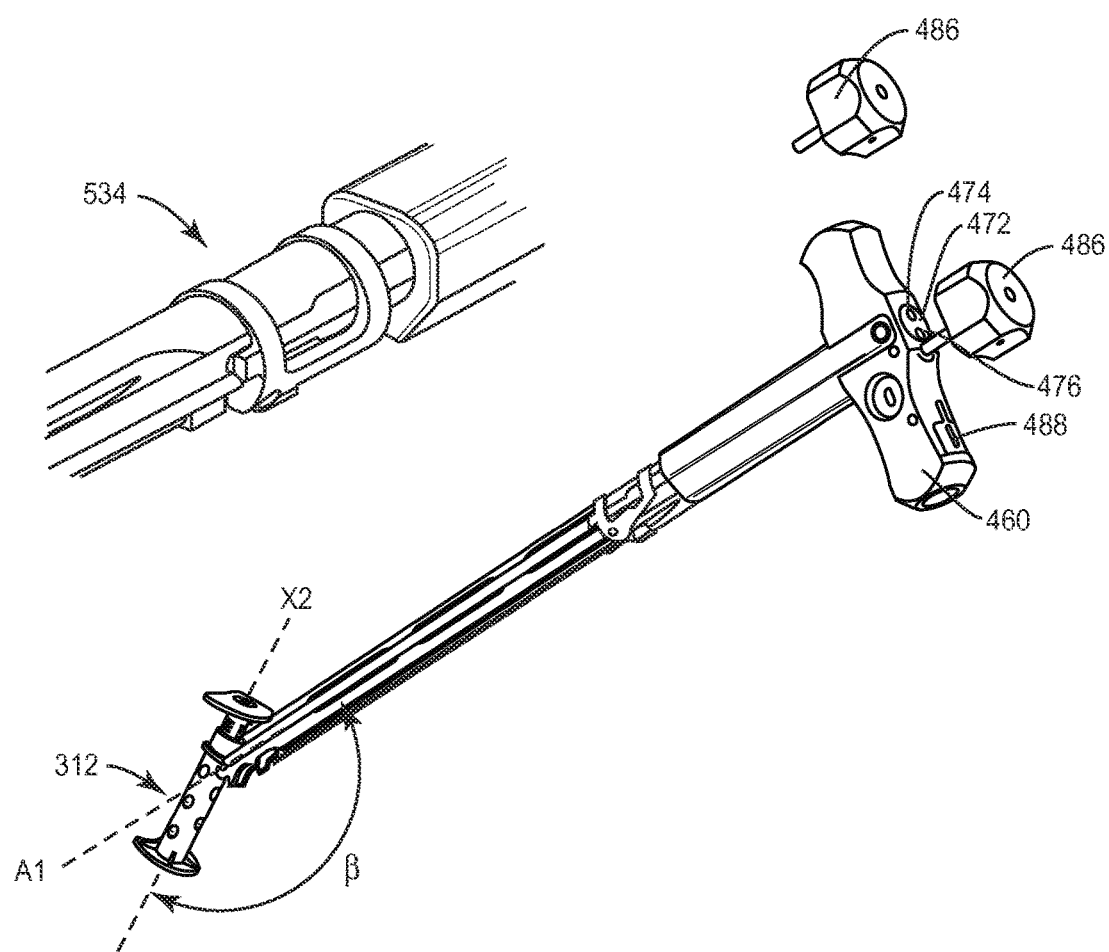
FIG. 20 illustrates perspective views of components of one embodiment of a surgical system in accordance with the principles of the present disclosure.
Figure 21:
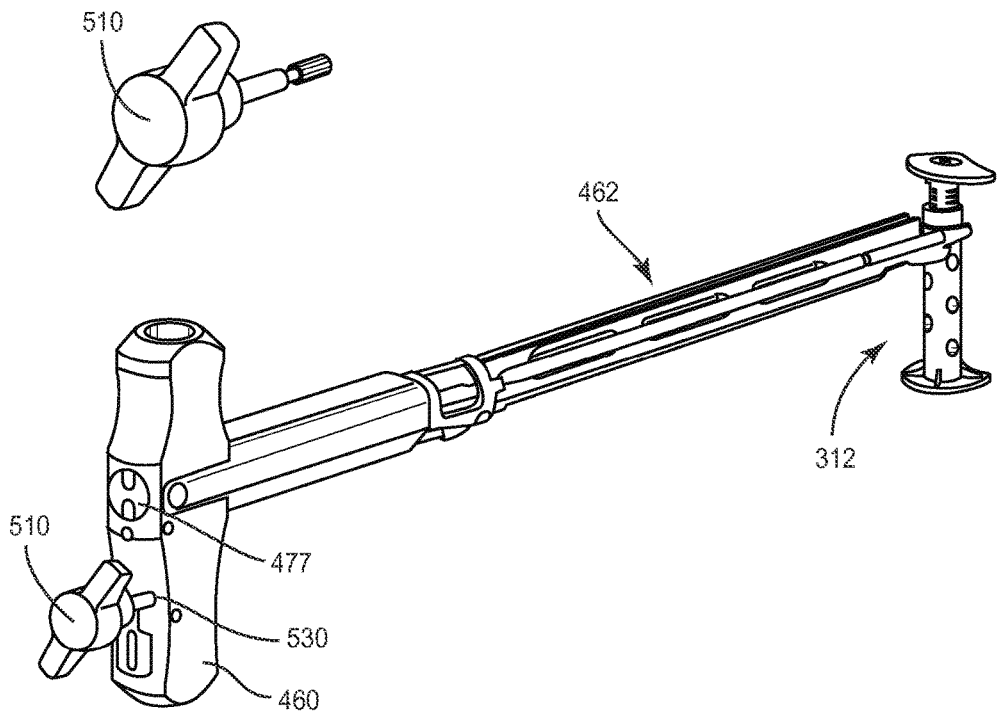
FIG. 21 illustrates perspective views of components of one embodiment of a surgical system in accordance with the principles of the present disclosure.
Figure 22:
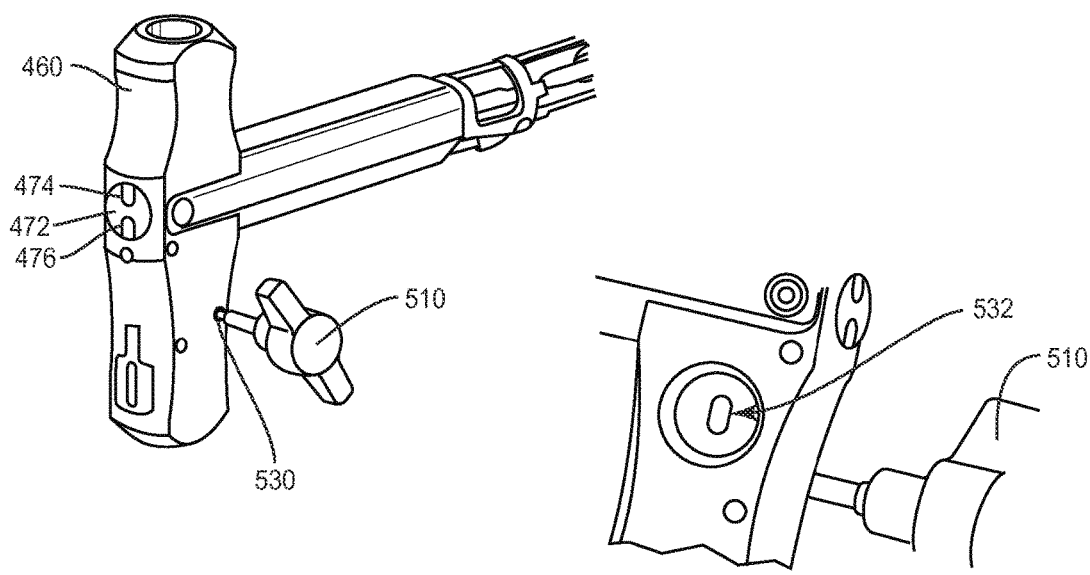
FIG. 22 illustrates perspective views of components of one embodiment of a surgical system in accordance with the principles of the present disclosure.
Figure 23:
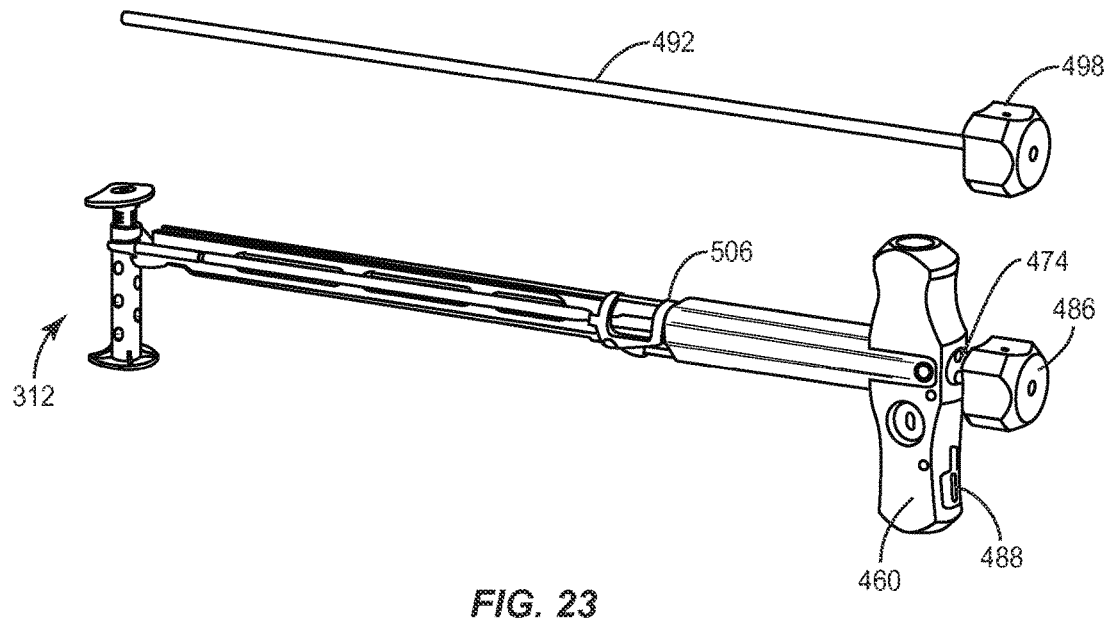
FIG. 23 is a perspective view of components of one embodiment of a surgical system in accordance with the principles of the present disclosure.
Figure 24:
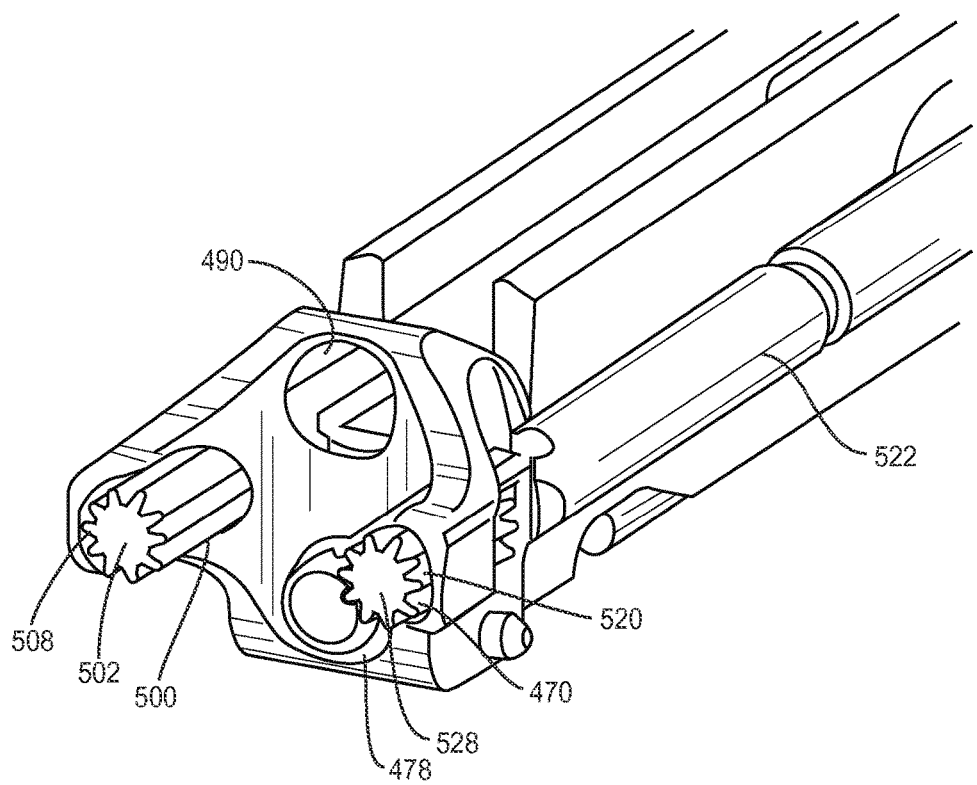
FIG. 24 is an enlarged, break away end view of components of the surgical system shown in FIG. 23.
Figure 25:
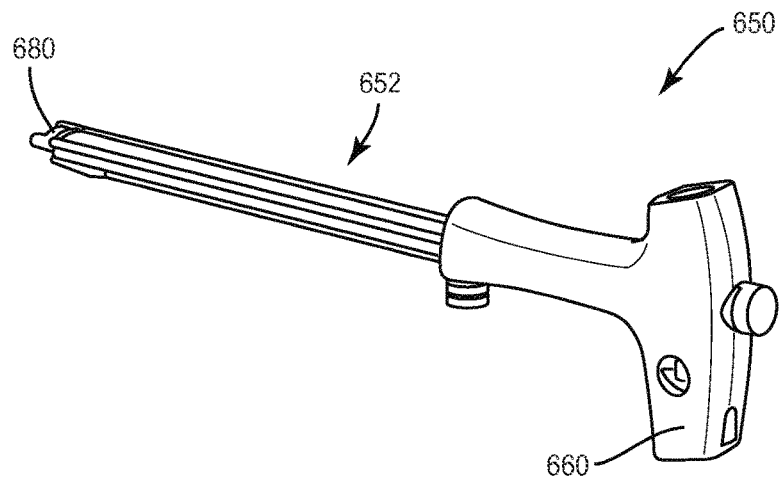
FIG. 25 is a perspective view of components of one embodiment of a surgical system in accordance with the principles of the present disclosure.
Figure 26:
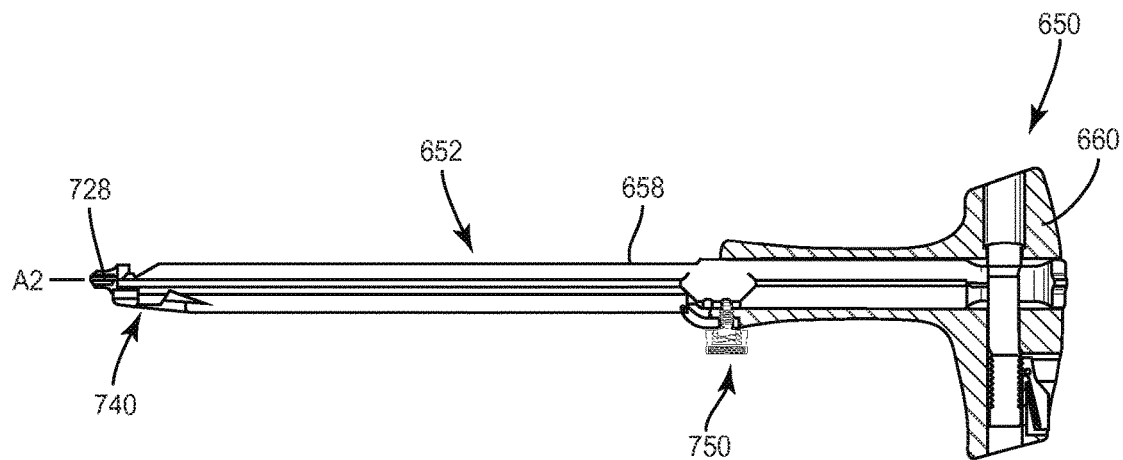
FIG. 26 is a side, cross section view of components of one embodiment of a surgical system in accordance with the principles of the present disclosure.

Inserter 450 includes linkage 540 configured to angle spinal implant 312 during implantation. Linkage 540 is connectable with gear portions 508, 528 such that gear portions 508, 528 are pivotable about axis A1 to pivot spinal implant 312. In some embodiments, linkage 540 is configured to rotate spinal implant 312 through an angle β relative to axis A1, as shown in FIG. 20. In some embodiments, angle β ranges from 0 to 60 degrees. Linkage 540 is actuated by an actuator, such as, for example, driver 486, as described herein.

In one embodiment, as shown in FIGS. 25-29, spinal implant system 10, similar to the systems and methods described with regard to FIGS. 14-24, includes spinal implant 312 engageable with an inserter 650, similar to inserter 450, described herein. Inserter 650 includes a body 652 that defines an axis A2. Body 652 includes a sleeve 658 and a handle 660.

Inserter 650 includes a shaft 680 configured for engagement with a portion of body 314 to releasably fix spinal implant 312 with inserter 650. Inserter 650 includes a driver 692 configured to engage lock 374, as described herein, to releasably fix lock 374 with spinal implant 312. Inserter 650 includes a driver 702 configured for expanding and contracting body 340 relative to body 314. Driver 702 includes a pinion gear portion 708 configured for engagement with teeth 364 of rack 362. Gear portion 708 is pivotable, as described herein, to facilitate angulation of spinal implant 312 during insertion, as described herein.

Inserter 650 includes a driver 722 configured for expanding and contracting body 340 relative to body 314 in conjunction with driver 702 for a dual gripping configuration. Driver 722 includes a pinion gear portion 728 configured for engagement with teeth 368 of rack 366. Gear portion 728 is pivotable to facilitate angulation of spinal implant 312 during insertion, as described herein.

Inserter 650 includes a linkage 740 configured to rotate spinal implant 312 during implantation. Linkage 740 is connectable with gear portions 708, 728 such that gear portions 708, 728 are pivotable about axis A1 to pivot spinal implant 312. In some embodiments, linkage 740 is configured to rotate spinal implant 312 through an angle relative to axis A2. Linkage 740 is actuated by an actuator, such as, for example, an index button 750. Index button 750 includes a base pin 752, a push sleeve pin 754, a spring washer 756 and a lock nut 758. Index button 750 is configured to engage linkage 740 to pivot gear portions 708, 728. Index button 750 is configured to facilitate dismantling of inserter 650 for cleaning. In some embodiments, index button 750 is disengaged from inserter 650 via an instrument, such as, for example a lateral knob to facilitate separation of components of insert 650, as shown in FIG. 27.

Figure 30:
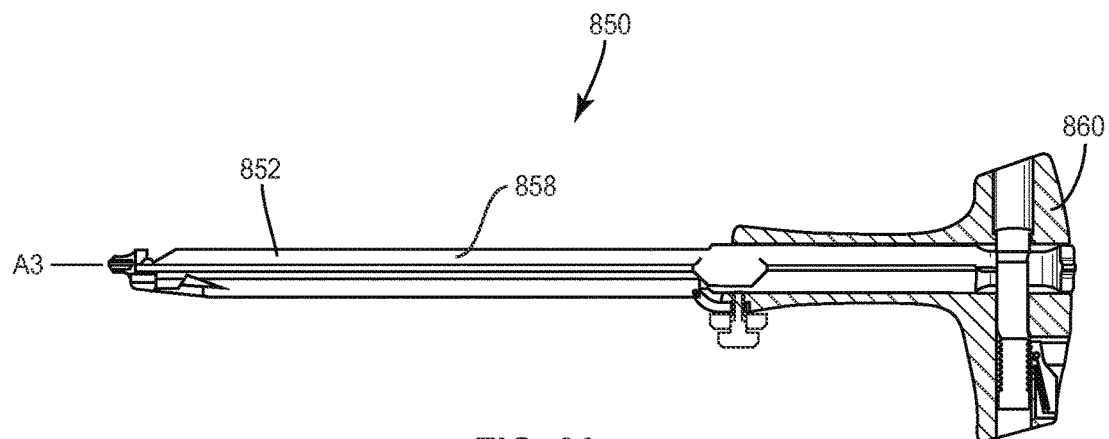
FIG. 30 is a side, cross section view of components of one embodiment of a surgical system in accordance with the principles of the present disclosure.
Figure 31:
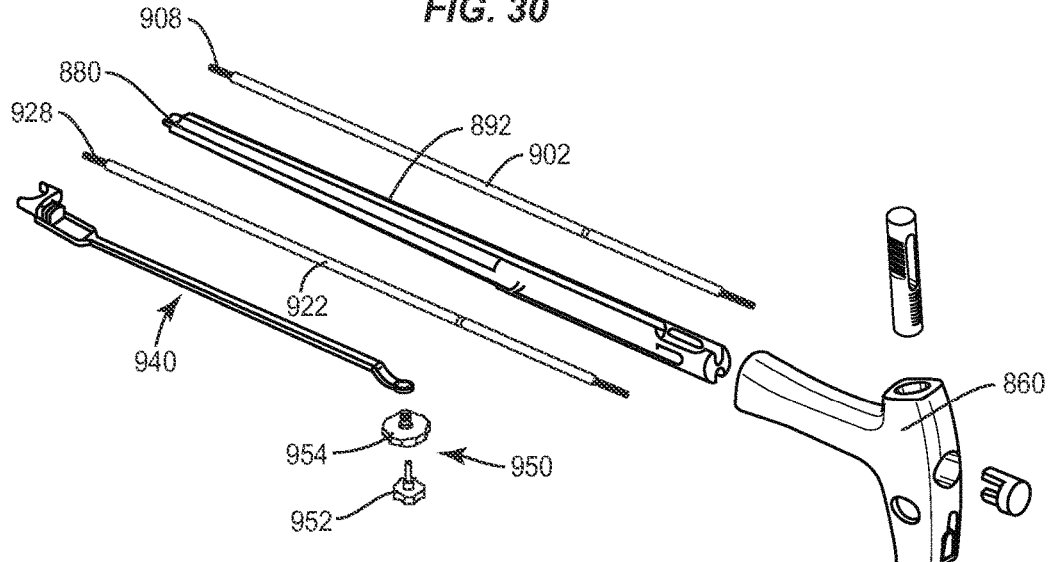
FIG. 31 is a perspective view of components of one embodiment of a surgical system in accordance with the principles of the present disclosure with parts separated.
Figure 32:
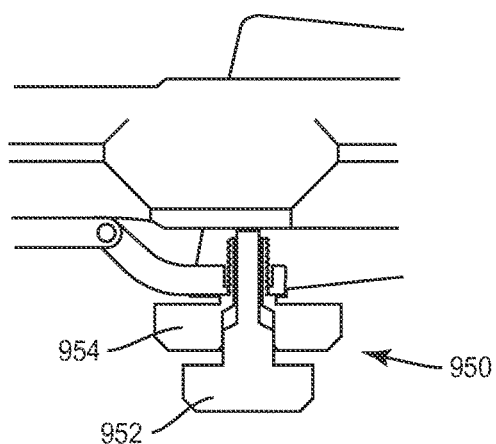
FIG. 32 is a break away cross section view of components of the surgical system shown in FIG. 30.

In one embodiment, as shown in FIGS. 30-32, spinal implant system 10, similar to the systems and methods described herein, includes spinal implant 312 engageable with an inserter 850, similar to inserter 450 described herein. Inserter 850 includes a body 852 that defines an axis A3. Body 852 includes a sleeve 858 and a handle 860.

Inserter 850 includes a shaft 880 configured for engagement with a portion of body 314 to releasably fix spinal implant 312 with inserter 850. Inserter 850 includes a driver 892 configured to engage lock 374, as described herein, to releasably fix lock 374 with spinal implant 312. Inserter 850 includes a driver 902 configured for expanding and contracting body 340 relative to body 314. Driver 902 includes a pinion gear portion 908 configured for engagement with teeth 364 of rack 362. Gear portion 908 is pivotable, as described herein, to facilitate angulation of spinal implant 312 during insertion, as described herein.

Inserter 850 includes a driver 922 configured for expanding and contracting body 340 relative to body 314 in conjunction with driver 902 for a dual gripping configuration. Driver 922 includes a pinion gear portion 928 configured for engagement with teeth 368 of rack 366. Gear portion 928 is pivotable to facilitate angulation of spinal implant 312 during insertion, as described herein.

Inserter 850 includes a linkage 940 configured to rotate spinal implant 312 during implantation. Linkage 940 is connectable with gear portions 908, 928 such that gear portions 908, 928 are pivotable about axis A3 to pivot spinal implant 312. In some embodiments, linkage 940 is configured to rotate spinal implant 312 through an angle relative to axis A3. Linkage 940 is connected to and actuated by an actuator, such as, for example, an index button 950. Index button 950 includes a pressure screw 952 and an assembling screw 954. Manipulation of index button 950 is configured to engage linkage 940 to pivot gear portions 908, 928 and fix gear portions 908, 928 in an orientation relative to axis A3. Index button 950 is configured to facilitate dismantling of inserter 850 for cleaning.

Figure 33:
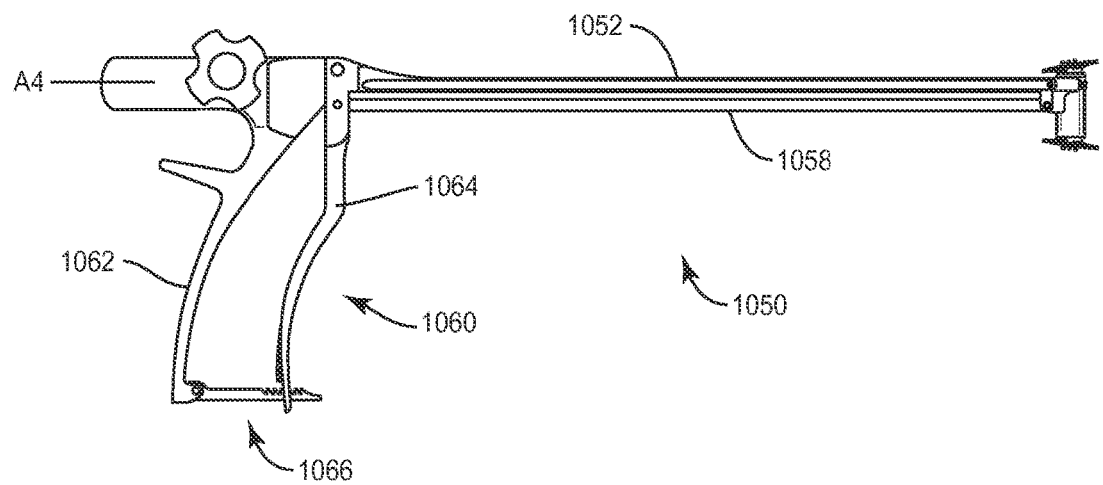
FIG. 33 is a side view of components of one embodiment of a surgical system in accordance with the principles of the present disclosure.
Figure 34:
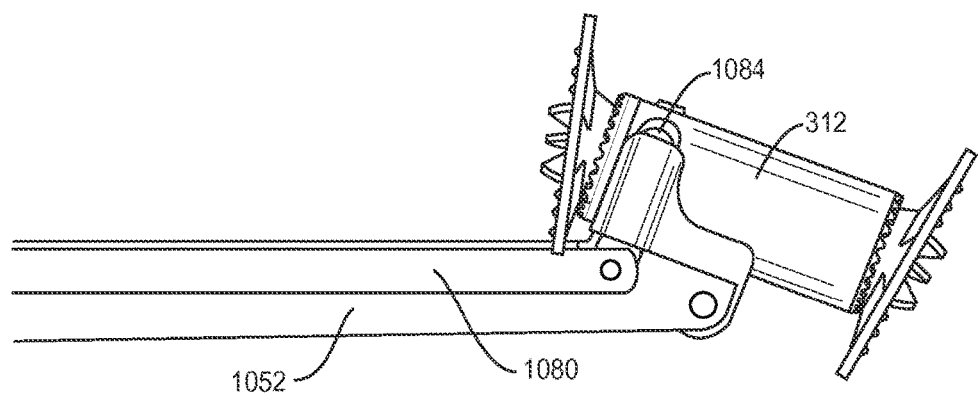
FIG. 34 is a break away view of components of one embodiment of a surgical system in accordance with the principles of the present disclosure.
Figure 35:
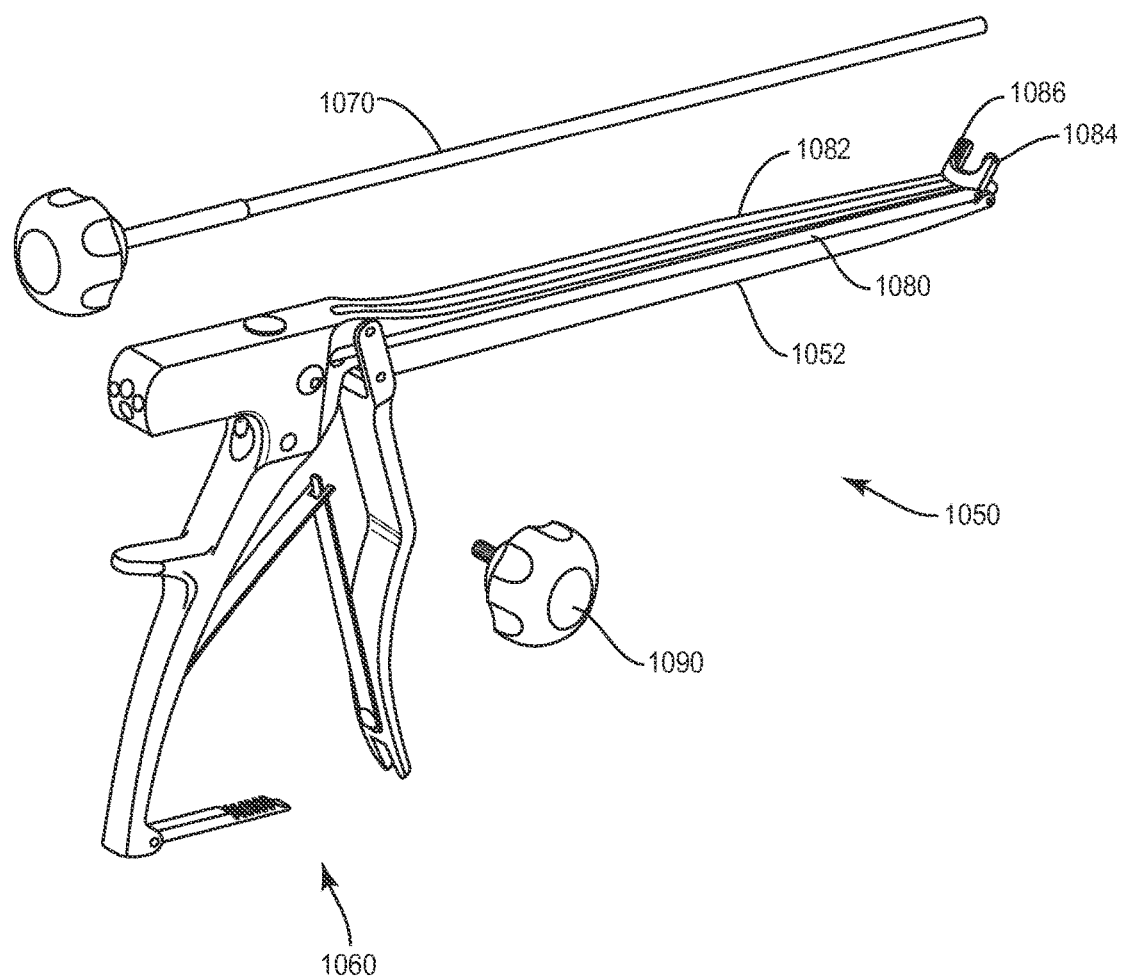
FIG. 35 is a perspective view of components of one embodiment of a surgical system in accordance with the principles of the present disclosure with parts separated.
Figure 36:
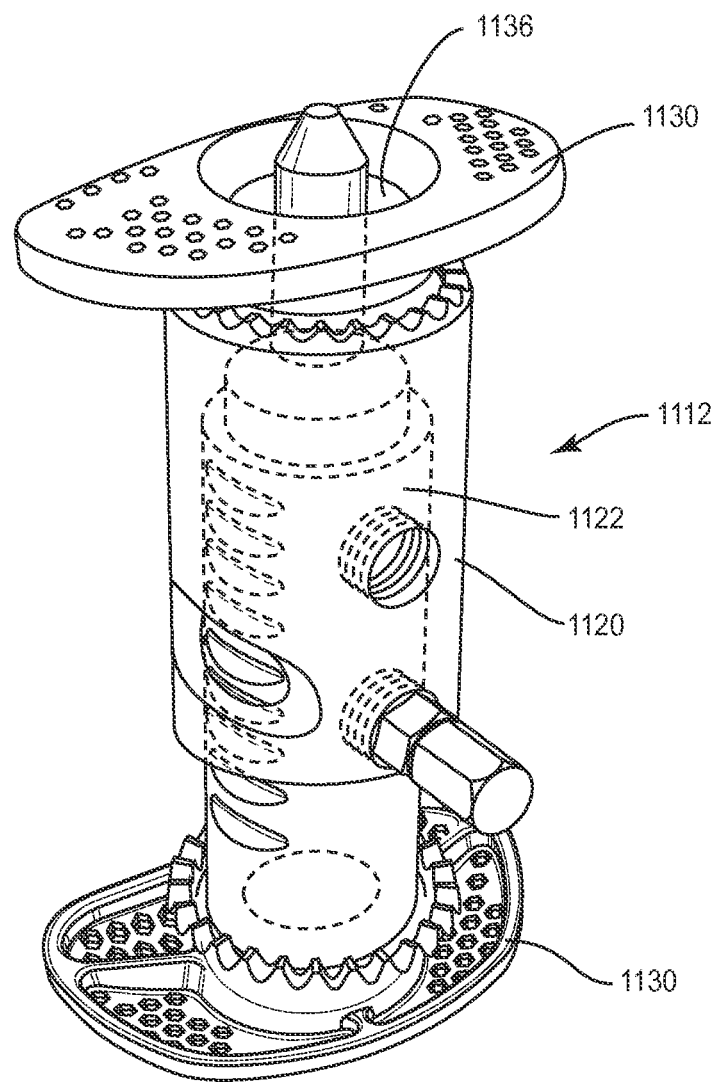
FIG. 36 is a perspective view of components of one embodiment of a surgical system in accordance with the principles of the present disclosure.
Figure 37:
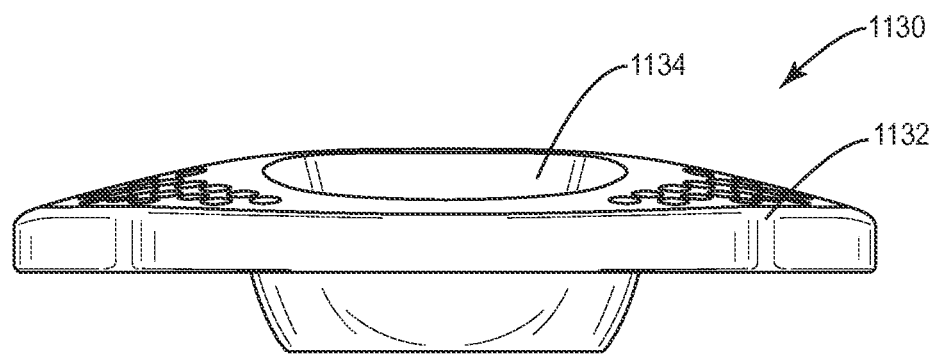
FIG. 37 is a side view of components of one embodiment of a surgical system in accordance with the principles of the present disclosure.
Figure 38:
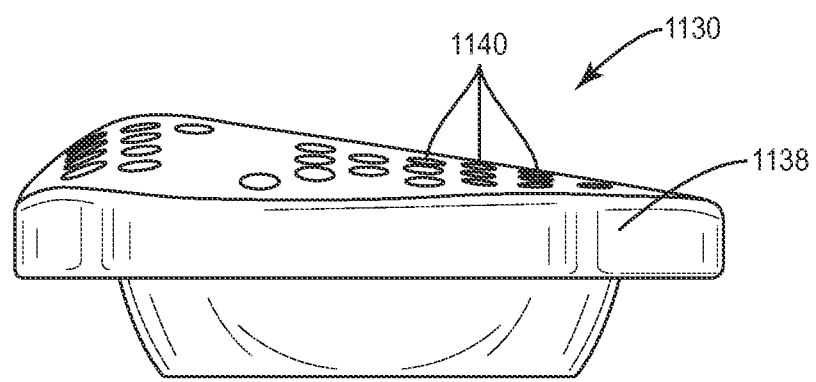
FIG. 38 is a side view of components of the surgical system shown in FIG. 37.
Figure 39:
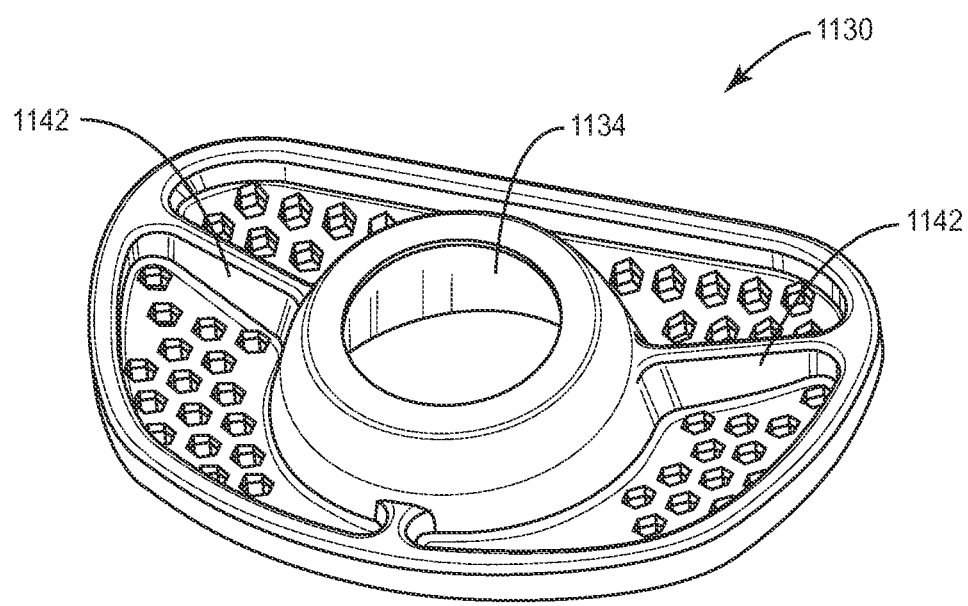
FIG. 39 is perspective view of components of the surgical system shown in FIG. 37.

In one embodiment, as shown in FIGS. 33-35, spinal implant system 10, similar to the systems and methods described herein, includes spinal implant 312 engageable with an inserter 1050, similar to inserter 450 described herein. Inserter 1050 includes a body 1052 that defines an axis A4. Inserter 1050 facilitates insertion of spinal implant 312 at an oblique angle for minimally invasive approaches.

Body 1052 includes a sleeve 1058 and a handle 1060. Handle 1060 includes a pistol grip configuration. Handle 1060 includes a grip portion 1062 and a lever 1064. Handle 1060 includes a ratchet 1066 configured to facilitate incremental translation of lever 1064 relative to grip portion 1062.

Inserter 1050 includes a dual purpose driver 1070 configured for engagement with a portion of body 314 to releasably fix spinal implant 312 with inserter 1050 and configured to engage lock 374, as described herein, to releasably fix lock 374 with spinal implant 312. Inserter 1050 includes drivers 1080, 1082 configured for expanding and contracting body 340 relative to body 314. Drivers 1080, 1082 each include a pinion gear portion 1084, 1086 configured for engagement with teeth 364 of rack 362. Gear portions 1084, 1086 are pivotable, as described herein, to facilitate angulation of spinal implant 312 during insertion, as described herein and shown in FIG. 34. Gear portions 1084, 1086 are actuated by a lateral knob 1090 to expand and contract spinal implant 312, similar to that described herein.

In some embodiments, as shown in FIGS. 36-39, spinal implant system 10, similar to the systems and methods described herein, includes a spinal implant 1112. Spinal implant 1112 includes a body 1120 and a body 1122, similar to that described herein, configured for relative contraction and/or expansion when disposed with vertebrae. Spinal implant 1112 includes endplates, such as, for example, anatomically configured endplate 1130. In some embodiments, the anatomic configuration can include undulations, arcuate portions, planar portions, angled portions, offset portions, staggered portions and/or preselected geometry corresponding to an endplate surface, cortical surface and/or cancellous surface of tissue.

Endplate 1130 includes a stratum 1132. Stratum 1132 includes at least one mating element, such as, for example, an opening 1134 configured for engagement with body 1120 and/or body 1122 to form a ball and socket joint 1136. In some embodiments, the mating elements can include biasing members, clips, key/keyway/keyslot, dovetail, tongue/groove, male/female, pin/groove, threaded, barbs, hooks and/or adhesive. In some embodiments, endplate 1130 is rotatable about and relative to an axis of body 1120 and/or body 1122 via joint 1136, similar to that described herein and is moveable in a plurality of angular orientations. In some embodiments, stratum 1132 includes a surface 1138 that defines a plurality of openings, such as, for example, hex holes 1140 configured to facilitate bone to bone contact at a selected fusion rate. In some embodiments, stratum 1132 includes a plurality of ribs 1142 configured to enhance stiffness of endplate 1130.

Figure 40:
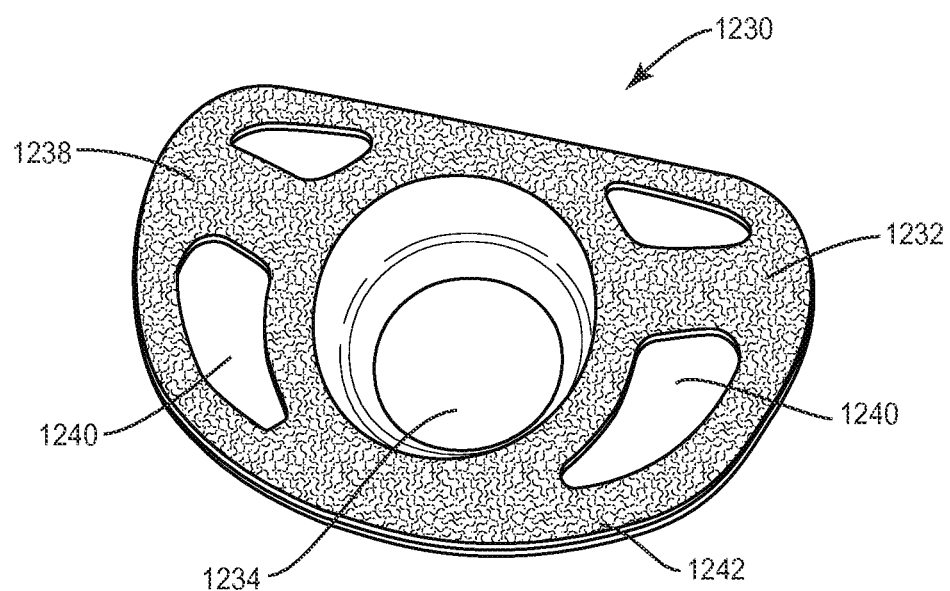
FIG. 40 is a perspective view of components of one embodiment of a surgical system in accordance with the principles of the present disclosure.
Figure 41:
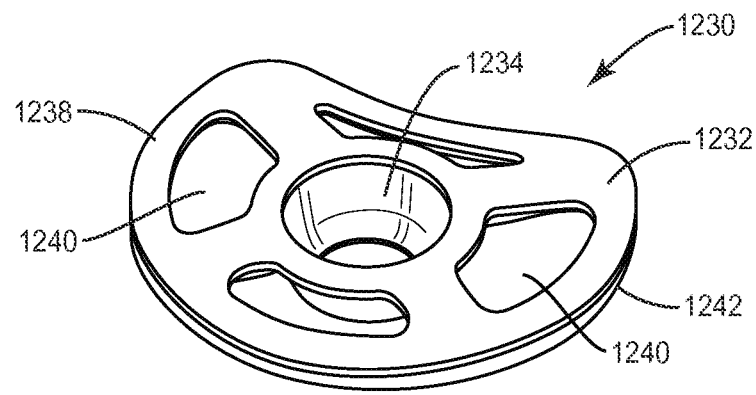
FIG. 41 is a perspective view of components of one embodiment of a surgical system in accordance with the principles of the present disclosure.

In some embodiments, as shown in FIGS. 40 and 41, spinal implant system 10, similar to the systems and methods described herein, includes endplates 1230. Endplate 1230 includes a stratum 1232. Stratum 1232 includes at least one mating element, similar to that described herein and such as, for example, an opening 1234 configured for engagement with body 1120 and/or body 1122, as described herein, to form a ball and socket joint, as described herein. In some embodiments, stratum 1232 includes a surface 1238 that defines a plurality of openings, such as, for example, windows 1240 configured to facilitate bone to bone contact at a fusion rate. In some embodiments, endplate 1230 includes a porous region 1242 and a solid region 1244.

Figure 42:
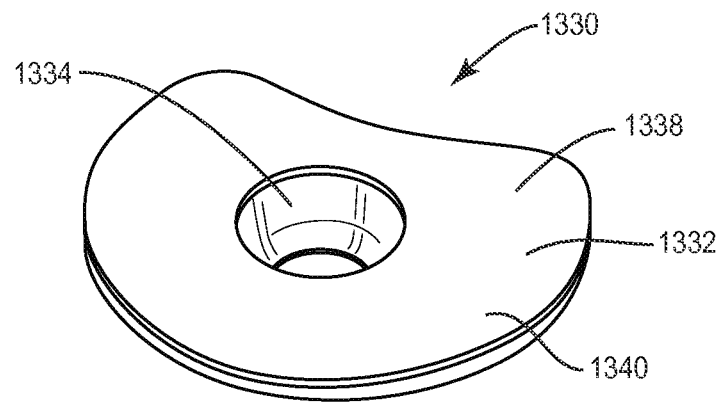
FIG. 42 is a perspective view of components of one embodiment of a surgical system in accordance with the principles of the present disclosure.
Figure 43:
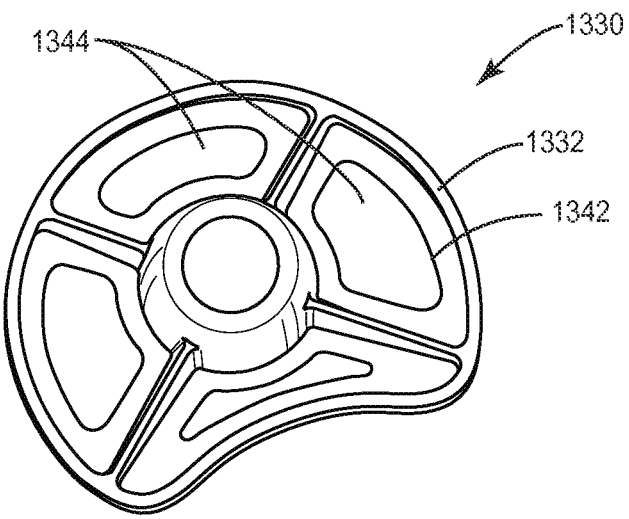
FIG. 43 is a perspective view of components of one embodiment of a surgical system in accordance with the principles of the present disclosure.

In some embodiments, as shown in FIGS. 42 and 43, spinal implant system 10, similar to the systems and methods described herein, includes endplates 1330. Endplate 1330 includes a stratum 1332. Stratum 1332 includes at least one mating element, similar to that described herein and such as, for example, an opening 1334 configured for engagement with body 1120 and/or body 1122, as described herein, to form a ball and socket joint, as described herein. In some embodiments, stratum 1332 includes a surface 1338 that defines a solid region 1340. Stratum 1332 includes a surface 1342 that defines a porous region 1344 disposed about surface 1342. In some embodiments, solid region 1340 and porous region 1344 comprise different thicknesses.

Figure 44:
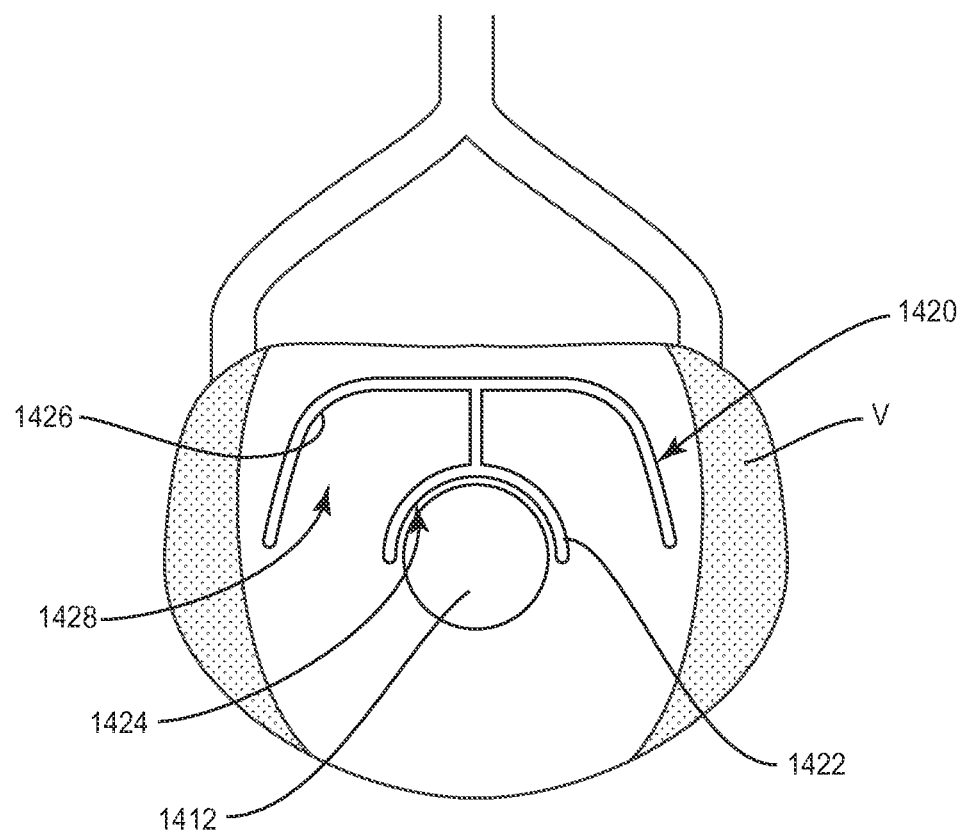
FIG. 44 is a plan view of components of one embodiment of a surgical system in accordance with the principles of the present disclosure.

In one embodiment, as shown in FIG. 44, spinal implant system 10, similar to the systems and methods described herein, includes a spinal implant 1412, similar to the spinal implants described herein, which is configured for relative expansion and/or contraction when disposed with vertebrae V, similar to that described herein. In some embodiments, spinal implant 1412 may include a fixed height and not expandable.

Spinal implant 1412 includes a receptacle, such as, for example, a container 1420 configured for disposal of agents, such as, for example, bone graft to facilitate insertion of bone graft with and/or circumferentially about spinal implant 1412. Container 1420 includes a surface 1422 that defines a cavity 1424 configured for disposal of spinal implant 1412. Container 1420 includes a surface 1426 that defines a cavity 1428 configured for disposal of bone graft.

In some embodiments, container 1420 is movable and/or adjustable relative to spinal implant 1412. In some embodiments, container 1420 is translatable in an anterior-posterior direction for movement and/or adjustment relative to spinal implant 1412. In some embodiments, container 1420 is in-situ attachable with spinal implant 1412 and comprises a bone graft partition for attachment with spinal implant 1412. In some embodiments, container 1420 is attached with spinal implant 1412 to maintain bone graft with spinal implant 1412 and resist and/or prevent bone graft from migrating out to a posterior side of the spine after a corpectomy procedure.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A spinal implant system comprising:
   a spinal implant comprising a first member defining a longitudinal axis and including a wall that defines an axial cavity, the first member further defining at least one lateral cavity oriented transverse relative to the longitudinal axis, the spinal implant comprising a second member including an axial surface defining gear teeth and being configured for disposal with the axial cavity such that the teeth are offset from the longitudinal axis; and
   a surgical instrument defining a longitudinal axis that is aligned with the at least one lateral cavity for engagement with the teeth to axially translate the second member relative to the first member,
   wherein the at least one lateral cavity includes a lateral aperture for disposal of a first pinion gear shaft of the surgical instrument and a contra-lateral aperture for disposal of a second pinion gear shaft of the surgical instrument.

2. A spinal implant system as recited in claim 1, wherein the wall includes an outer surface and the lateral aperture is disposed with the outer surface.

3. A spinal implant system as recited in claim 1, wherein the wall includes an outer surface and the lateral aperture and the contra-lateral aperture are disposed with the outer surface.

4. A spinal implant system as recited in claim 1, wherein the members axially translate between a contracted configuration and an expanded configuration for disposal in a selected orientation.

5. A spinal implant system as recited in claim 1, wherein the members are axially translatable from a contracted configuration to an expanded configuration for disposal in a selected orientation, and/or an expanded configuration to a contracted configuration for disposal in a selected orientation.

6. A spinal implant system as recited in claim 1, wherein the second member is axially translatable relative to the first member in a first direction for disposal in a selected orientation and/or a second, opposite direction for disposal in a selected orientation.

7. A spinal implant as recited in claim 1, further comprising a lock engageable with the members to fix the members in a selected orientation.

8. A spinal implant system as recited in claim 1, wherein the instrument is engageable with the members to provisionally fix the members in a selected orientation.

9. A spinal implant system as recited in claim 1, wherein at least one of the members includes a mating element engageable with an endplate of a plurality of alternate endplates such that the member is interchangeable with the plurality of endplates.

10. A spinal implant system as recited in claim 9, wherein at least one of the plurality of alternate endplates includes a non-planar surface configuration.

11. A spinal implant system as recited in claim 1, wherein at least one of the members includes an endplate rotatable to one or a plurality of axial orientations relative to the longitudinal axis.

12. A spinal implant system as recited in claim 1, wherein the second member includes a rack comprising the teeth.

13. A spinal implant system as recited in claim 1, wherein the surgical instrument comprises linkage that is connectable with the pinion gear shafts such that the pinion gear shafts are pivotable about the longitudinal axis of the surgical instrument to pivot the spinal implant.

14. A spinal implant system comprising:
   a spinal implant including a first member defining a longitudinal axis and at least one lateral cavity oriented transverse relative to the longitudinal axis, and a second member including offset gear teeth; and
   a surgical instrument defining a longitudinal axis that is aligned with the at least one lateral cavity for engagement with the teeth to axially translate the second member relative to the first member,
   wherein the at least one lateral cavity includes a lateral aperture for disposal of a first pinion gear shaft of the surgical instrument and a contra-lateral aperture for disposal of a second pinion gear shaft of the surgical instrument.

15. A spinal implant system as recited in claim 14, wherein the surgical instrument is connected with the spinal implant to rotate the spinal implant relative to the longitudinal axis of the surgical instrument.

16. A spinal implant system as recited in claim 14, wherein the surgical instrument is connected with the spinal implant in rotate the spinal implant relative in the longitudinal axis of the surgical instrument between an insertion configuration and an implant orientation.

17. A spinal implant system as recited in claim 14, wherein the surgical instrument includes a handle having a pistol grip configuration.

18. A spinal implant system as recited in claim 14, wherein the surgical instrument includes a plurality of passageways disposed in alignment with the longitudinal axis of the surgical instrument, the first pinion gear shaft being disposed in one of the passageways for engagement with the teeth to axially translate the second member relative to the first member and the second pinion gear shaft rotates the spinal implant relative to the longitudinal axis of the surgical instrument.

19. A spinal implant system as recited in claim 14, further comprising a lock engageable with the members to fix the members in a selected orientation, the lock having a reduced diameter portion including a frangible torque limit.

20. A spinal implant system comprising:
- a spinal implant including a first member defining at least one lateral cavity and a second member including offset gear teeth, wherein at least one of the members includes a mating element engageable with an endplate of a plurality of alternate endplates such that the member is interchangeable with the plurality of endplates; and
- a surgical instrument defining a longitudinal axis that is aligned with the at least one lateral cavity to axially translate the second member relative to the first member,
- wherein the at least one lateral cavity includes a lateral aperture for disposal of a first pinion gear shaft of the surgical instrument and a contra-lateral aperture for disposal of a second pinion gear shaft of the surgical instrument.

* * * * *

UNITED STATES PATENT AND TRADEMARK OFFICE
CERTIFICATE OF CORRECTION

PATENT NO. : 9,757,250 B2  
APPLICATION NO. : 14/853691  
DATED : September 12, 2017  
INVENTOR(S) : Josse et al.

Page 1 of 1

It is certified that error appears in the above-identified patent and that said Letters Patent is hereby corrected as shown below:

On the Title Page

In item (72), under "Inventors", in Column 1, Line 1, delete "Yens Vaud" and insert -- Yens, Vaud --, therefor.

In item (72), under "Inventors", in Column 1, Line 3, delete "Jorg" and insert -- Jörg --, therefor.

In the Specification

In Column 2, Line 43, delete "disclosure:" and insert -- disclosure; --, therefor.

In Column 15, Line 47, delete "tangibly" and insert -- frangibly --, therefor.

In Column 17, Line 1, delete "tangibly" and insert -- frangibly --, therefor.

In Column 20, Line 51, delete "dips," and insert -- clips, --, therefor.

In the Claims

In Column 28, Line 10, in Claim 7, delete "implant" and insert -- implant system --, therefor.

In Column 28, Line 56, in Claim 16, delete "in rotate the spinal implant relative in" and insert -- to rotate the spinal implant relative to --, therefor.

Signed and Sealed this  
Eighteenth Day of September, 2018

Andrei Iancu  
*Director of the United States Patent and Trademark Office*